US008691878B2

(12) United States Patent
Rosenberg et al.

(10) Patent No.: US 8,691,878 B2
(45) Date of Patent: *Apr. 8, 2014

(54) SOLID PHARMACEUTICAL DOSAGE FORM

(71) Applicant: AbbVie Inc., North Chicago, IL (US)

(72) Inventors: Jeorg Rosenberg, Ellerstadt (DE); Ulrich Reinhold, Heidelberg (DE); Bernd Liepold, Dossenheim (DE); Gunther Berndl, Herxheim (DE); Joerg Breitenbach, Mannheim (DE); Laman Alani, Foster City, CA (US); Soumojeet Ghosh, Lansdale, PA (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,799

(22) Filed: Nov. 12, 2012

(65) Prior Publication Data

US 2013/0072508 A1 Mar. 21, 2013

Related U.S. Application Data

(60) Continuation of application No. 12/880,781, filed on Sep. 13, 2010, now Pat. No. 8,309,613, which is a division of application No. 10/925,442, filed on Aug. 25, 2004, now Pat. No. 8,025,899.

(60) Provisional application No. 60/498,412, filed on Aug. 28, 2003.

(51) Int. Cl.
*A61K 8/72* (2006.01)
*A61K 9/20* (2006.01)
*A61K 9/48* (2006.01)
*A61K 31/425* (2006.01)

(52) U.S. Cl.
USPC ........ 514/772; 514/274; 514/772.3; 514/937; 424/455; 424/464; 424/484; 424/486

(58) Field of Classification Search
USPC ............... 514/271, 772, 772.3, 937, 272; 424/455, 464, 484, 486
See application file for complete search history.

(56) References Cited

U.S. PATENT DOCUMENTS

| | | | |
|---|---|---|---|
| 4,540,602 A | 9/1985 | Motoyama et al. |
| 4,590,065 A | 5/1986 | Piechota, Jr. et al. |
| 4,620,974 A | 11/1986 | Hersh et al. |
| 4,758,427 A | 7/1988 | Leeson |
| 4,769,235 A | 9/1988 | Schlesinger et al. |
| 4,769,236 A | 9/1988 | Panoz et al. |
| 4,801,460 A | 1/1989 | Goertz et al. |
| 4,804,699 A | 2/1989 | Nelson et al. |
| 4,806,337 A | 2/1989 | Snipes et al. |
| 4,851,438 A | 7/1989 | Flashinski |
| 4,880,585 A | 11/1989 | Klimesch et al. |
| 4,904,699 A | 2/1990 | Bauer |
| 4,957,681 A | 9/1990 | Klimesch et al. |
| 4,996,058 A | 2/1991 | Sinnreich |
| 5,028,433 A | 7/1991 | Ishimaru et al. |
| 5,073,379 A | 12/1991 | Klimesch et al. |
| 5,145,683 A | 9/1992 | Rhodes |
| 5,281,420 A | 1/1994 | Kelm et al. |
| 5,368,864 A | 11/1994 | Lahr et al. |
| 5,403,923 A | 4/1995 | Kashimura et al. |
| 5,405,616 A | 4/1995 | Wunderlich et al. |
| 5,456,923 A | 10/1995 | Nakamichi et al. |
| 5,476,667 A | 12/1995 | Kristensen et al. |
| 5,484,926 A | 1/1996 | Dressman et al. |
| 5,490,990 A | 2/1996 | Grabowski et al. |
| 5,501,858 A | 3/1996 | Fuisz |
| 5,525,628 A | 6/1996 | Nicola et al. |
| 5,541,206 A | 7/1996 | Kempf et al. |
| 5,545,628 A | 8/1996 | Deboeck et al. |
| 5,552,159 A | 9/1996 | Mueller et al. |
| 5,559,158 A | 9/1996 | Al-Razzak et al. |
| 5,567,823 A | 10/1996 | Tien et al. |
| 5,585,397 A | 12/1996 | Tung et al. |
| 5,610,193 A | 3/1997 | Al-Razzak et al. |
| 5,635,523 A | 6/1997 | Kempf et al. |
| 5,641,516 A | 6/1997 | Grabowski et al. |
| 5,648,497 A | 7/1997 | Kempf et al. |
| 5,654,003 A | 8/1997 | Fuisz et al. |
| 5,674,882 A | 10/1997 | Kempf et al. |
| 5,695,784 A | 12/1997 | Pollinger et al. |
| 5,700,410 A | 12/1997 | Nakamichi et al. |
| 5,707,648 A | 1/1998 | Yiv |
| 5,725,878 A | 3/1998 | Al-Razzak et al. |
| 5,727,878 A | 3/1998 | Sullivan, Jr. |

(Continued)

FOREIGN PATENT DOCUMENTS

| | | |
|---|---|---|
| AU | 3113893 | 7/1993 |
| CA | 1270201 A1 | 6/1990 |

(Continued)

OTHER PUBLICATIONS

Anastasiadou C., et al., "Solid Dispersions: Comparison of Prepared Melts and Coprecipitates of Diazepam and Polyoxyethylene Glycol 4000," Drug Development and Industrial Pharmacy, 1983, vol. 9 (1-2), pp. 103-115.

(Continued)

*Primary Examiner* — San-Ming Hui
*Assistant Examiner* — Kathrien Cruz
(74) *Attorney, Agent, or Firm* — Bradley E. Davis

(57) ABSTRACT

A solid pharmaceutical dosage form providing improved oral bioavailability is disclosed for inhibitors of HIV protease. In particular, the dosage form comprises a solid dispersion of at least one HIV protease inhibitor and at least one pharmaceutically acceptable water-soluble polymer and at least one pharmaceutically acceptable surfactant, said pharmaceutically acceptable water-soluble polymer having a Tg of at least about 50° C. Preferably, the pharmaceutically acceptable surfactant has an HLB value of from about 4 to about 10.

20 Claims, No Drawings

(56) References Cited

U.S. PATENT DOCUMENTS

| | | |
|---|---|---|
| 5,741,519 A | 4/1998 | Rosenberg et al. |
| 5,756,450 A | 5/1998 | Hahn et al. |
| 5,762,961 A | 6/1998 | Roser et al. |
| 5,773,025 A | 6/1998 | Baichwal |
| 5,776,495 A | 7/1998 | Duclos et al. |
| 5,834,472 A | 11/1998 | Sangekar et al. |
| 5,852,195 A | 12/1998 | Romines et al. |
| 5,858,401 A | 1/1999 | Bhalani et al. |
| 5,889,051 A | 3/1999 | Chen et al. |
| 5,897,910 A | 4/1999 | Rosenberg et al. |
| 5,914,332 A | 6/1999 | Sham et al. |
| 5,935,936 A | 8/1999 | Fasbender et al. |
| 5,939,099 A | 8/1999 | Grabowski et al. |
| 5,945,123 A | 8/1999 | Hermelin |
| 5,945,127 A | 8/1999 | Breitenbach et al. |
| 5,948,426 A | 9/1999 | Jefferies |
| 5,948,436 A | 9/1999 | Al-Razzak et al. |
| 5,955,475 A | 9/1999 | Krape et al. |
| 5,958,452 A | 9/1999 | Oshlack et al. |
| 5,958,455 A | 9/1999 | Roser et al. |
| 5,965,161 A | 10/1999 | Oshlack et al. |
| 5,965,163 A | 10/1999 | Miller et al. |
| 5,969,181 A | 10/1999 | Breitenbach et al. |
| 6,001,391 A | 12/1999 | Zeidler et al. |
| 6,009,690 A | 1/2000 | Rosenberg et al. |
| 6,027,747 A | 2/2000 | Terracol et al. |
| 6,037,157 A | 3/2000 | Norbeck et al. |
| 6,042,847 A | 3/2000 | Kerc et al. |
| 6,045,829 A | 4/2000 | Liversidge et al. |
| 6,051,253 A | 4/2000 | Zettler et al. |
| 6,063,821 A | 5/2000 | Breitenbach et al. |
| 6,066,334 A | 5/2000 | Kolter et al. |
| 6,071,539 A | 6/2000 | Robinson et al. |
| 6,083,518 A | 7/2000 | Lindahl |
| 6,113,941 A | 9/2000 | Takada et al. |
| 6,120,802 A | 9/2000 | Breitenbach et al. |
| 6,132,659 A | 10/2000 | Rosenberg et al. |
| 6,136,346 A | 10/2000 | Eljamal et al. |
| 6,150,424 A | 11/2000 | Breitenbach et al. |
| 6,162,467 A | 12/2000 | Miller et al. |
| 6,187,342 B1 | 2/2001 | Zeidler et al. |
| 6,197,781 B1 | 3/2001 | Guitard et al. |
| 6,197,787 B1 | 3/2001 | Franson et al. |
| 6,207,197 B1 | 3/2001 | Illum et al. |
| 6,221,368 B1 | 4/2001 | Breitenbach et al. |
| 6,221,399 B1 | 4/2001 | Rolfes et al. |
| 6,221,400 B1 | 4/2001 | Liversidge et al. |
| 6,232,333 B1 | 5/2001 | Lipari et al. |
| 6,248,363 B1 | 6/2001 | Patel et al. |
| 6,248,775 B1 | 6/2001 | Vazquez et al. |
| 6,251,434 B1 | 6/2001 | Breitenbach et al. |
| 6,261,599 B1 | 7/2001 | Oshlack et al. |
| 6,264,981 B1 | 7/2001 | Zhang et al. |
| 6,267,985 B1 | 7/2001 | Chen et al. |
| 6,268,207 B1 | 7/2001 | Bailey |
| 6,271,307 B1 | 8/2001 | Huff et al. |
| 6,274,727 B1 | 8/2001 | Maul et al. |
| 6,281,282 B1 | 8/2001 | Breitenbach et al. |
| 6,284,270 B1 | 9/2001 | Lagoviyer et al. |
| 6,284,803 B1 | 9/2001 | Kothrade et al. |
| 6,290,990 B1 | 9/2001 | Grabowski et al. |
| 6,294,192 B1 | 9/2001 | Patel et al. |
| 6,309,663 B1 | 10/2001 | Patel et al. |
| 6,312,726 B1 | 11/2001 | Nakamichi et al. |
| 6,318,650 B1 | 11/2001 | Breitenbach et al. |
| 6,319,520 B1 | 11/2001 | Wuthrich et al. |
| 6,322,816 B1 | 11/2001 | Zeidler et al. |
| 6,333,048 B1 | 12/2001 | Asmussen et al. |
| 6,350,398 B1 | 2/2002 | Breitenbach et al. |
| 6,372,259 B1 | 4/2002 | Kumar |
| 6,372,905 B1 | 4/2002 | Chemburkar et al. |
| 6,379,707 B2 | 4/2002 | Vladyka, Jr. et al. |
| 6,383,471 B1 | 5/2002 | Chen et al. |
| 6,387,401 B2 | 5/2002 | Rosenberg et al. |
| 6,391,338 B1 | 5/2002 | Frisbee et al. |
| 6,423,256 B1 | 7/2002 | Kothrade et al. |
| 6,436,440 B1 | 8/2002 | Meffert et al. |
| 6,440,946 B1 | 8/2002 | Kiso et al. |
| 6,451,339 B2 | 9/2002 | Patel et al. |
| 6,462,093 B1 | 10/2002 | Miyamoto et al. |
| 6,465,010 B1 | 10/2002 | Lagoviyer et al. |
| 6,465,011 B2 | 10/2002 | Law et al. |
| 6,488,939 B1 | 12/2002 | Zeidler et al. |
| 6,488,961 B1 | 12/2002 | Robinson et al. |
| 6,488,963 B1 | 12/2002 | McGinity et al. |
| 6,497,905 B1 | 12/2002 | Vladyka, Jr. et al. |
| 6,511,681 B2 | 1/2003 | Vladyka, Jr. et al. |
| 6,528,089 B1 | 3/2003 | Kothrade et al. |
| 6,541,030 B2 | 4/2003 | Vaghefi |
| 6,541,034 B1 | 4/2003 | Gergely et al. |
| 6,547,997 B1 | 4/2003 | Breitenbach et al. |
| 6,569,455 B1 | 5/2003 | Kanikanti et al. |
| 6,576,255 B1 | 6/2003 | Petereit et al. |
| 6,579,521 B2 | 6/2003 | Sahner |
| 6,599,528 B1 | 7/2003 | Rosenberg et al. |
| 6,599,931 B1 | 7/2003 | Breitenbach et al. |
| 6,608,198 B2 | 8/2003 | Dickman et al. |
| 6,610,764 B1 | 8/2003 | Martin et al. |
| 6,632,389 B1 | 10/2003 | Ernst et al. |
| 6,632,455 B2 | 10/2003 | Sangekar et al. |
| 6,649,186 B1 | 11/2003 | Robinson et al. |
| 6,669,879 B1 | 12/2003 | Spengler et al. |
| 6,669,883 B1 | 12/2003 | Rosenberg et al. |
| 6,677,362 B1 | 1/2004 | Ghebre-Sellassie et al. |
| 6,692,767 B2 | 2/2004 | Burnside et al. |
| 6,703,403 B2 | 3/2004 | Norbeck et al. |
| 6,706,281 B2 | 3/2004 | Oshlack et al. |
| 6,706,283 B1 | 3/2004 | Appel et al. |
| 6,713,081 B2 | 3/2004 | Robinson et al. |
| 6,730,319 B2 | 5/2004 | Maeder et al. |
| 6,733,781 B2 | 5/2004 | Abu-Izza et al. |
| 6,737,005 B1 | 5/2004 | Rosenberg et al. |
| 6,743,442 B2 | 6/2004 | Oshlack et al. |
| 6,763,607 B2 | 7/2004 | Beyerinck et al. |
| 6,787,157 B1 | 9/2004 | Rosenberg et al. |
| 6,805,881 B1 | 10/2004 | Kanikanti et al. |
| 6,834,310 B2 | 12/2004 | Munger et al. |
| 6,872,336 B2 | 3/2005 | Tanno et al. |
| 6,894,171 B1 | 5/2005 | Bauer et al. |
| 6,899,899 B2 | 5/2005 | Takagi et al. |
| 6,923,988 B2 | 8/2005 | Patel et al. |
| 6,973,741 B2 | 12/2005 | Beyerinck et al. |
| 6,982,094 B2 | 1/2006 | Sowden |
| 7,014,810 B2 | 3/2006 | Krull et al. |
| 7,022,344 B1 | 4/2006 | Kothrade et al. |
| 7,122,143 B2 | 10/2006 | Sowden et al. |
| 7,148,359 B2 | 12/2006 | Chemburkar et al. |
| 7,229,641 B2 | 6/2007 | Cherukuri |
| 7,235,260 B2 | 6/2007 | Crew et al. |
| 7,282,218 B2 | 10/2007 | Kulkarni et al. |
| 7,297,345 B2 | 11/2007 | Sowden |
| 7,364,752 B1 | 4/2008 | Fort et al. |
| 7,407,670 B2 | 8/2008 | Six et al. |
| 7,413,690 B1 | 8/2008 | Cheboyina et al. |
| 7,419,685 B2 | 9/2008 | Kothrade et al. |
| 7,491,407 B2 | 2/2009 | Pourdeyhimi et al. |
| 7,550,158 B2 | 6/2009 | Appel et al. |
| 7,645,474 B1 | 1/2010 | Pathak et al. |
| 7,687,071 B1 | 3/2010 | Heger et al. |
| 7,727,551 B2 | 6/2010 | Massironi |
| 7,771,632 B2 | 8/2010 | Ghebre-Sellassie et al. |
| 7,780,988 B2 | 8/2010 | Beyerinck et al. |
| 7,785,512 B1 | 8/2010 | Pathak |
| 7,846,477 B2 | 12/2010 | Rosenberg et al. |
| 7,867,517 B2 | 1/2011 | Massironi |
| 7,887,840 B2 | 2/2011 | Curatolo et al. |
| 7,923,026 B2 | 4/2011 | Moschwitzer |
| 7,951,401 B2 | 5/2011 | Colombo et al. |
| 7,968,120 B2 | 6/2011 | Li et al. |
| 7,972,624 B2 | 7/2011 | Li et al. |
| 8,025,899 B2 | 9/2011 | Berndl et al. |
| 8,268,349 B2 | 9/2012 | Rosenberg et al. |
| 2001/0006650 A1 | 7/2001 | Burnside et al. |
| 2001/0006677 A1 | 7/2001 | McGinity et al. |

(56) References Cited

U.S. PATENT DOCUMENTS

| | | |
|---|---|---|
| 2001/0038852 A1 | 11/2001 | Kolter et al. |
| 2001/0039551 A1 | 11/2001 | Saito et al. |
| 2001/0044409 A1 | 11/2001 | Ghebre-Sellassie et al. |
| 2001/0048946 A1 | 12/2001 | Ghebre-Sellassie |
| 2001/0051721 A1 | 12/2001 | Dickman et al. |
| 2002/0001617 A1 | 1/2002 | Lee et al. |
| 2002/0006443 A1 | 1/2002 | Curatolo et al. |
| 2002/0009494 A1 | 1/2002 | Curatolo et al. |
| 2002/0015731 A1 | 2/2002 | Appel et al. |
| 2002/0031547 A1 | 3/2002 | Takagi et al. |
| 2002/0044968 A1 | 4/2002 | Van Lengerich |
| 2002/0102300 A1 | 8/2002 | Miller et al. |
| 2002/0114833 A1 | 8/2002 | Abu-Izza et al. |
| 2002/0122825 A1 | 9/2002 | Hinrichs et al. |
| 2002/0142043 A1 | 10/2002 | Kato et al. |
| 2002/0160042 A1 | 10/2002 | Petereit et al. |
| 2002/0161884 A1 | 10/2002 | Munger et al. |
| 2002/0187188 A1 | 12/2002 | Cherukuri |
| 2002/0198160 A1 | 12/2002 | Everitt et al. |
| 2003/0015814 A1 | 1/2003 | Krull et al. |
| 2003/0021840 A1 | 1/2003 | Infeld et al. |
| 2003/0021842 A1 | 1/2003 | Lagoviyer et al. |
| 2003/0039686 A1 | 2/2003 | Maeder et al. |
| 2003/0054038 A1 | 3/2003 | Crew et al. |
| 2003/0059468 A1 | 3/2003 | Mattern et al. |
| 2003/0064108 A1 | 4/2003 | Lukas et al. |
| 2003/0072801 A1 | 4/2003 | Curatolo et al. |
| 2003/0086976 A1 | 5/2003 | Hayes et al. |
| 2003/0091626 A1 | 5/2003 | Katsuta |
| 2003/0091630 A1 | 5/2003 | Louie-Helm et al. |
| 2003/0091643 A1 | 5/2003 | Friesen et al. |
| 2003/0096791 A1 | 5/2003 | Gupte et al. |
| 2003/0099690 A1 | 5/2003 | Awamura et al. |
| 2003/0099703 A1 | 5/2003 | Aoki |
| 2003/0099708 A1 | 5/2003 | Rowe et al. |
| 2003/0104063 A1 | 6/2003 | Babcock et al. |
| 2003/0104065 A1 | 6/2003 | Brodin et al. |
| 2003/0104068 A1 | 6/2003 | Mathiowitz et al. |
| 2003/0109639 A1 | 6/2003 | Lippold et al. |
| 2003/0129250 A1 | 7/2003 | Batycky et al. |
| 2003/0133984 A1 | 7/2003 | Ambühl et al. |
| 2003/0141378 A1 | 7/2003 | Raehse et al. |
| 2003/0147965 A1 | 8/2003 | Bassett et al. |
| 2003/0152619 A1 | 8/2003 | Stevens et al. |
| 2003/0153608 A1 | 8/2003 | Maegerlein et al. |
| 2003/0161884 A1 | 8/2003 | Rosenberg et al. |
| 2003/0170309 A1 | 9/2003 | Babcock et al. |
| 2003/0203027 A1 | 10/2003 | Verreck et al. |
| 2003/0206947 A1 | 11/2003 | Kanikanti et al. |
| 2003/0206978 A1 | 11/2003 | Sherwood et al. |
| 2003/0211168 A1 | 11/2003 | Lynenskjold et al. |
| 2003/0211197 A1 | 11/2003 | Burkle et al. |
| 2003/0212102 A1 | 11/2003 | Koretke et al. |
| 2003/0219489 A1 | 11/2003 | Curatolo et al. |
| 2003/0224043 A1 | 12/2003 | Appel et al. |
| 2003/0228358 A1 | 12/2003 | Perlman et al. |
| 2004/0001888 A1 | 1/2004 | Jin |
| 2004/0009222 A1 | 1/2004 | Chou et al. |
| 2004/0013697 A1 | 1/2004 | Berndl et al. |
| 2004/0013734 A1 | 1/2004 | Babcock et al. |
| 2004/0013735 A1 | 1/2004 | Martin-Letellier et al. |
| 2004/0013736 A1 | 1/2004 | Nakano et al. |
| 2004/0014817 A1 | 1/2004 | Rosenberg et al. |
| 2004/0024031 A1 | 2/2004 | Morissette et al. |
| 2004/0029892 A1 | 2/2004 | Rosenberg et al. |
| 2004/0044196 A1 | 3/2004 | Davidson et al. |
| 2004/0062778 A1 | 4/2004 | Shefer et al. |
| 2004/0062802 A1 | 4/2004 | Hermelin |
| 2004/0067256 A1 | 4/2004 | Juppo |
| 2004/0076673 A1 | 4/2004 | Bateman et al. |
| 2004/0081694 A1 | 4/2004 | Oshlack et al. |
| 2004/0081701 A1 | 4/2004 | Erkoboni et al. |
| 2004/0086569 A1 | 5/2004 | Sparer et al. |
| 2004/0091529 A1 | 5/2004 | Edgren et al. |
| 2004/0096499 A1 | 5/2004 | Vaya et al. |
| 2004/0104501 A1 | 6/2004 | Petereit et al. |
| 2004/0110694 A1 | 6/2004 | Ghebre-Sellassie et al. |
| 2004/0115256 A1 | 6/2004 | MacAllister et al. |
| 2004/0115273 A1 | 6/2004 | Sparer et al. |
| 2004/0120927 A1 | 6/2004 | Nathan |
| 2004/0138231 A1 | 7/2004 | Bateman et al. |
| 2004/0146550 A1 | 7/2004 | Ng et al. |
| 2004/0151056 A1 | 8/2004 | Omtveit et al. |
| 2004/0154317 A1 | 8/2004 | Shekunov et al. |
| 2004/0156894 A1 | 8/2004 | Grother et al. |
| 2004/0156905 A1 | 8/2004 | Babcock et al. |
| 2004/0166153 A1 | 8/2004 | McAllister et al. |
| 2004/0185112 A1 | 9/2004 | Beyerinck et al. |
| 2004/0185170 A1 | 9/2004 | Chungi et al. |
| 2004/0194338 A1 | 10/2004 | Beyerinck et al. |
| 2004/0197411 A1 | 10/2004 | Gao et al. |
| 2004/0197414 A1 | 10/2004 | Ahola et al. |
| 2004/0198645 A1 | 10/2004 | Ambuhl et al. |
| 2004/0198901 A1 | 10/2004 | Graham et al. |
| 2004/0219222 A1 | 11/2004 | Sjoblom |
| 2004/0220081 A1 | 11/2004 | Kreitz et al. |
| 2004/0228916 A1 | 11/2004 | Tanno et al. |
| 2004/0234597 A1 | 11/2004 | Shefer et al. |
| 2004/0234673 A1 | 11/2004 | Letavernier et al. |
| 2004/0247624 A1 | 12/2004 | Unger et al. |
| 2004/0247666 A1 | 12/2004 | Massironi |
| 2004/0247687 A1 | 12/2004 | Petereit et al. |
| 2004/0253314 A1 | 12/2004 | Petereit et al. |
| 2004/0258752 A1 | 12/2004 | Paruthi et al. |
| 2004/0265378 A1 | 12/2004 | Peng et al. |
| 2005/0003004 A1 | 1/2005 | Vehring et al. |
| 2005/0008697 A1 | 1/2005 | Gorissen |
| 2005/0008706 A1 | 1/2005 | Holm et al. |
| 2005/0013856 A1 | 1/2005 | Trivedi et al. |
| 2005/0014304 A1 | 1/2005 | Moon et al. |
| 2005/0025791 A1 | 2/2005 | Remenar et al. |
| 2005/0031691 A1 | 2/2005 | McGurk et al. |
| 2005/0031692 A1 | 2/2005 | Beyerinck et al. |
| 2005/0031693 A1 | 2/2005 | Babcock et al. |
| 2005/0031696 A1 | 2/2005 | Kolhe et al. |
| 2005/0042293 A1 | 2/2005 | Jackson et al. |
| 2005/0048112 A1 | 3/2005 | Breitenbach et al. |
| 2005/0048116 A1 | 3/2005 | Straub et al. |
| 2005/0058705 A1 | 3/2005 | Remon et al. |
| 2005/0058710 A1 | 3/2005 | Straub et al. |
| 2005/0079138 A1 | 4/2005 | Chickering, III et al. |
| 2005/0084529 A1 | 4/2005 | Rosenberg et al. |
| 2005/0089568 A1 | 4/2005 | Oshlack et al. |
| 2005/0100586 A1 | 5/2005 | Sournac et al. |
| 2005/0100598 A1 | 5/2005 | Mizumoto et al. |
| 2005/0106257 A1 | 5/2005 | Albayrak |
| 2005/0143404 A1 | 6/2005 | Rosenberg et al. |
| 2005/0158385 A1 | 7/2005 | Verreck et al. |
| 2005/0158386 A1 | 7/2005 | Tanno et al. |
| 2005/0163852 A1 | 7/2005 | Bresciani et al. |
| 2005/0163853 A1 | 7/2005 | Szente et al. |
| 2005/0169988 A1 | 8/2005 | Tao et al. |
| 2005/0175687 A1 | 8/2005 | McAllister et al. |
| 2005/0202090 A1 | 9/2005 | Clarke |
| 2005/0245483 A1 | 11/2005 | Brogmann et al. |
| 2005/0281876 A1 | 12/2005 | Li et al. |
| 2006/0003011 A1 | 1/2006 | Crew et al. |
| 2006/0003942 A1 | 1/2006 | Tung et al. |
| 2006/0013869 A1 | 1/2006 | Ignatious et al. |
| 2006/0029678 A1 | 2/2006 | Deghenghi |
| 2006/0034887 A1 | 2/2006 | Pelissier |
| 2006/0051412 A1 | 3/2006 | Petereit et al. |
| 2006/0073203 A1 | 4/2006 | Ljusberg-Wahren et al. |
| 2006/0078609 A1 | 4/2006 | Vandecruys et al. |
| 2006/0115539 A1 | 6/2006 | Prasch |
| 2006/0134203 A1 | 6/2006 | Ambuhl et al. |
| 2006/0147538 A1 | 7/2006 | Craig et al. |
| 2006/0177496 A1 | 8/2006 | McAllister et al. |
| 2006/0204577 A1 | 9/2006 | Crew et al. |
| 2006/0216351 A1 | 9/2006 | Friesen et al. |
| 2006/0251724 A1 | 11/2006 | Farrell et al. |
| 2006/0257470 A1 | 11/2006 | Rosenberg et al. |
| 2006/0269608 A1 | 11/2006 | Abu Shmeis-Ziadeh et al. |
| 2006/0286169 A1 | 12/2006 | Leigh et al. |

(56) References Cited

U.S. PATENT DOCUMENTS

| | | |
|---|---|---|
| 2007/0009592 A1 | 1/2007 | Remon et al. |
| 2007/0014856 A1 | 1/2007 | Takagi et al. |
| 2007/0031501 A1 | 2/2007 | Van Es et al. |
| 2007/0042044 A1 | 2/2007 | Fischer et al. |
| 2007/0053978 A1 | 3/2007 | Sherwood et al. |
| 2007/0077305 A1 | 4/2007 | Le et al. |
| 2007/0098795 A1 | 5/2007 | Miller et al. |
| 2007/0122482 A1 | 5/2007 | Holm et al. |
| 2007/0134336 A1 | 6/2007 | Worle et al. |
| 2007/0249643 A1 | 10/2007 | Rosenberg et al. |
| 2007/0249692 A1 | 10/2007 | Fort et al. |
| 2007/0275058 A1 | 11/2007 | Tanaka et al. |
| 2007/0287664 A1 | 12/2007 | Ralston, II et al. |
| 2007/0298116 A1 | 12/2007 | Bechtold-Peters et al. |
| 2008/0038340 A1 | 2/2008 | Kusaki et al. |
| 2008/0063708 A1 | 3/2008 | Perlman et al. |
| 2008/0138419 A1 | 6/2008 | Liao et al. |
| 2008/0153925 A1 | 6/2008 | Pierobon et al. |
| 2008/0181948 A1 | 7/2008 | Berndl et al. |
| 2008/0187612 A1 | 8/2008 | Kannar et al. |
| 2008/0199516 A1 | 8/2008 | McAllister |
| 2008/0206349 A1 | 8/2008 | Barnwell et al. |
| 2008/0206350 A1 | 8/2008 | Gryczke |
| 2008/0213371 A1 | 9/2008 | Jain et al. |
| 2008/0234352 A1 | 9/2008 | Fischer et al. |
| 2008/0241261 A1 | 10/2008 | Kolter et al. |
| 2008/0248107 A1 | 10/2008 | Pilgaonkar et al. |
| 2008/0254124 A1 | 10/2008 | Bar-Shalom |
| 2008/0260814 A1 | 10/2008 | Petereit et al. |
| 2008/0260835 A1 | 10/2008 | Hayes et al. |
| 2008/0292707 A1 | 11/2008 | Babcock et al. |
| 2008/0299203 A1 | 12/2008 | Rosenberg |
| 2008/0305168 A1 | 12/2008 | Moon et al. |
| 2008/0317851 A1 | 12/2008 | Appel et al. |
| 2009/0011024 A1 | 1/2009 | Babcock et al. |
| 2009/0017125 A1 | 1/2009 | Lynenskjold et al. |
| 2009/0036551 A1 | 2/2009 | Venkatesh et al. |
| 2009/0053317 A1 | 2/2009 | Vigo et al. |
| 2009/0104269 A1 | 4/2009 | Graham et al. |
| 2009/0148517 A1 | 6/2009 | Oshlack et al. |
| 2009/0218731 A1 | 9/2009 | Rogasch et al. |
| 2009/0258953 A1 | 10/2009 | Dobrawa et al. |
| 2009/0263479 A1 | 10/2009 | Moschwitzer et al. |
| 2009/0304795 A1 | 12/2009 | Bernigal et al. |
| 2009/0324694 A1 | 12/2009 | Mohammad |
| 2010/0010101 A1 | 1/2010 | Cherukuri |
| 2010/0062073 A1 | 3/2010 | Beyerinck et al. |
| 2010/0068268 A1 | 3/2010 | Rahmouni et al. |
| 2010/0112050 A1 | 5/2010 | Ryoo et al. |
| 2010/0137455 A1 | 6/2010 | Bouillo et al. |
| 2010/0166857 A1 | 7/2010 | Yan et al. |
| 2010/0172974 A1 | 7/2010 | Oshlack et al. |
| 2010/0179182 A1 | 7/2010 | Shmeis et al. |
| 2010/0204259 A1 | 8/2010 | Tygesen et al. |
| 2010/0204425 A1 | 8/2010 | Mertoglu et al. |
| 2010/0215753 A1 | 8/2010 | Sherwood et al. |
| 2010/0222220 A1 | 9/2010 | Hanna et al. |
| 2010/0247612 A1 | 9/2010 | Fuisz |
| 2010/0256110 A1 | 10/2010 | Babcock et al. |
| 2011/0008430 A1 | 1/2011 | Rosenberg et al. |
| 2011/0015216 A1 | 1/2011 | Berndl et al. |
| 2011/0020455 A1 | 1/2011 | Yoshida et al. |
| 2011/0091546 A1 | 4/2011 | Tanaka et al. |
| 2011/0123652 A1 | 5/2011 | Berndl et al. |
| 2011/0217381 A1 | 9/2011 | Angus et al. |
| 2011/0236443 A1 | 9/2011 | Hall et al. |
| 2011/0244002 A1 | 10/2011 | Shen et al. |
| 2011/0250269 A1 | 10/2011 | Xu et al. |
| 2011/0277339 A1 | 11/2011 | Beyerinck et al. |
| 2011/0288181 A1 | 11/2011 | Koltzenburg et al. |
| 2011/0311595 A1 | 12/2011 | Berndl et al. |
| 2012/0022089 A1 | 1/2012 | Rosenberg |
| 2013/0004578 A1 | 1/2013 | Rosenberg |

FOREIGN PATENT DOCUMENTS

| | | |
|---|---|---|
| CA | 2096969 A1 | 5/1992 |
| CA | 2227272 A1 | 3/1997 |
| CA | 2343234 A | 3/2000 |
| CA | 2352874 A | 6/2000 |
| CA | 2367020 A | 9/2000 |
| CA | 2368625 A | 10/2000 |
| CA | 2374931 A | 1/2001 |
| CA | 2408915 A | 11/2002 |
| CA | 2479749 A | 10/2003 |
| CA | 2501245 A | 4/2004 |
| CA | 2568378 A | 12/2005 |
| CA | 2229650 C | 8/2006 |
| DE | 973095 C | 12/1959 |
| DE | 19536387 A1 | 4/1997 |
| DE | 19629753 A1 | 1/1998 |
| DE | 19637479 A1 | 3/1998 |
| EP | 0240904 A2 | 10/1987 |
| EP | 0240906 A2 | 10/1987 |
| EP | 252886 A2 | 1/1988 |
| EP | 0414422 A2 | 2/1991 |
| EP | 421581 A1 | 4/1991 |
| EP | 421582 A1 | 4/1991 |
| EP | 240906 B1 | 5/1991 |
| EP | 0435450 A2 | 7/1991 |
| EP | 0272336 B1 | 10/1991 |
| EP | 240904 B1 | 7/1992 |
| EP | 0570327 A1 | 11/1993 |
| EP | 358105 B1 | 3/1994 |
| EP | 414422 B1 | 4/1994 |
| EP | 732923 A1 | 9/1996 |
| EP | 0852140 A1 | 7/1998 |
| EP | 864324 A1 | 9/1998 |
| EP | 864326 A2 | 9/1998 |
| EP | 0942721 A1 | 9/1999 |
| EP | 0551820 B1 | 11/1999 |
| EP | 988106 A1 | 3/2000 |
| EP | 1003485 A1 | 5/2000 |
| EP | 1027886 A2 | 8/2000 |
| EP | 1027887 A2 | 8/2000 |
| EP | 1070496 A1 | 1/2001 |
| EP | 988106 B1 | 8/2001 |
| EP | 732923 B1 | 12/2001 |
| EP | 1175205 A2 | 1/2002 |
| EP | 1227797 A2 | 8/2002 |
| EP | 942721 B1 | 1/2003 |
| EP | 864324 B1 | 10/2003 |
| EP | 852140 B1 | 12/2003 |
| EP | 864326 B1 | 6/2004 |
| EP | 1227797 B1 | 1/2005 |
| EP | 1175205 B1 | 6/2006 |
| EP | 2311435 A1 | 4/2011 |
| GB | 2011382 A | 7/1979 |
| GB | 2053681 A | 2/1981 |
| GB | 2011382 B | 8/1982 |
| GB | 2173703 A | 10/1986 |
| JP | 61205208 A | 9/1986 |
| JP | 61243012 A | 10/1986 |
| JP | 6048920 A | 2/1994 |
| KR | 1019075252 A | 10/1999 |
| KR | 101999007525 A | 10/1999 |
| WO | 8905138 A1 | 6/1989 |
| WO | 9006115 A2 | 6/1990 |
| WO | 9118613 A1 | 12/1991 |
| WO | 9209614 A1 | 6/1992 |
| WO | 9307859 A1 | 4/1993 |
| WO | 9311749 A1 | 6/1993 |
| WO | 9315736 A1 | 8/1993 |
| WO | 9320138 A2 | 10/1993 |
| WO | 9507696 A1 | 3/1995 |
| WO | 9509614 A1 | 4/1995 |
| WO | 9522319 A1 | 8/1995 |
| WO | 9600179 A1 | 1/1996 |
| WO | 9619962 A1 | 7/1996 |
| WO | 9619963 A1 | 7/1996 |
| WO | 9623499 A1 | 8/1996 |
| WO | 9636318 A2 | 11/1996 |
| WO | 9701349 A1 | 1/1997 |

(56) References Cited

FOREIGN PATENT DOCUMENTS

| | | |
|---|---|---|
| WO | 9706781 A1 | 2/1997 |
| WO | 9713503 A1 | 4/1997 |
| WO | 9721685 A1 | 6/1997 |
| WO | 9734645 A1 | 9/1997 |
| WO | 9744014 A1 | 11/1997 |
| WO | 9746222 A1 | 12/1997 |
| WO | 9807429 A2 | 2/1998 |
| WO | 9822094 A2 | 5/1998 |
| WO | 9822106 A1 | 5/1998 |
| WO | 9824430 A1 | 6/1998 |
| WO | 9938496 A1 | 8/1999 |
| WO | 9955774 A1 | 11/1999 |
| WO | 9963841 A1 | 12/1999 |
| WO | 0000179 A1 | 1/2000 |
| WO | 0040220 A1 | 7/2000 |
| WO | 00/57855 A1 | 10/2000 |
| WO | 0057854 A2 | 10/2000 |
| WO | 00/64450 A1 | 11/2000 |
| WO | 0074677 A2 | 12/2000 |
| WO | 0100175 A1 | 1/2001 |
| WO | 0122938 A1 | 4/2001 |
| WO | 0123362 A2 | 4/2001 |
| WO | 0134118 A2 | 5/2001 |
| WO | 0134119 A2 | 5/2001 |
| WO | 0152821 A1 | 7/2001 |
| WO | 01/74787 A2 | 11/2001 |
| WO | 0191727 A2 | 12/2001 |
| WO | 0203955 A1 | 1/2002 |
| WO | 0205788 A1 | 1/2002 |
| WO | 0220057 A2 | 3/2002 |
| WO | 0235991 A2 | 5/2002 |
| WO | 0238126 A2 | 5/2002 |
| WO | 0245696 A1 | 6/2002 |
| WO | 02/087585 A1 | 7/2002 |
| WO | 02089835 A2 | 11/2002 |
| WO | 02092595 A1 | 11/2002 |
| WO | 02096395 A1 | 12/2002 |
| WO | 03006382 A1 | 1/2003 |
| WO | 03006383 A1 | 1/2003 |
| WO | 03047551 A1 | 6/2003 |
| WO | 03063833 A1 | 8/2003 |
| WO | 03/084462 A3 | 10/2003 |
| WO | 03080120 A1 | 10/2003 |
| WO | 2004032903 A2 | 4/2004 |
| WO | 2004039349 A1 | 5/2004 |
| WO | 2004050068 A1 | 6/2004 |
| WO | 2004054568 A1 | 7/2004 |
| WO | 2004062643 A1 | 7/2004 |
| WO | 2004100930 A1 | 11/2004 |
| WO | 2004112755 A1 | 12/2004 |
| WO | 2005004836 A2 | 1/2005 |
| WO | 2005007070 A2 | 1/2005 |
| WO | 2005007139 A2 | 1/2005 |
| WO | 2005035514 A2 | 4/2005 |
| WO | 2005039551 A2 | 5/2005 |
| WO | 2006091529 A2 | 8/2006 |
| WO | 2007002041 A2 | 1/2007 |
| WO | 2007050631 A2 | 5/2007 |
| WO | 2010017053 A1 | 2/2010 |
| WO | 2011090724 A2 | 7/2011 |
| WO | 2011159626 A1 | 12/2011 |
| ZA | 9608134 A | 3/1998 |
| ZA | 9708219 A | 3/1999 |

OTHER PUBLICATIONS

Bates T.R., "Dissolution Characteristics of Reserpine-Polyvinylpyrrolidone Co-Precipitates" in: Journal of Pharmacology, Letters to the Editor, 1969, vol. 21, pp. 710-712.

Breitenbach J., et al., "Melt-Extruded Molecular Dispersions," Pharmaceutical Extrusion Technology, 2003, vol. 13, pp. 245-260.

Breitenbach J., et al., "Solid Dispersions by an Integrated Melt Extrusion System," Proceed. Int'l. Symp. Control. Rel. Bioact. Mater., 1998, vol. 25, pp. 804-805.

Chatham S.M., "The Use of Bases in SSM Formulations," S.T.P. Pharma Pratiques, 1987, vol. 3 (7), pp. 575-582.

Chiang C.C., et al., "Formulation Development of an Oral Dosage Form for an HIV Protease Inhibitor, Ag1284," International Journal of Pharmaceutics, 1995, vol. 117 (2), pp. 197-207.

Co-Pending U.S. Appl. No. 12/880,766, filed Sep. 13, 2010.

Co-Pending U.S. Appl. No. 12/880,781, filed Sep. 13, 2010.

Craig D.Q., et al., "The Relevance of the Amorphous State to Pharmaceutical Dosage Forms: Glassy Drugs and Freeze Dried Systems," International Journal of Pharmaceutics, 1999, vol. 179 (2), pp. 179-207.

Datta S., et al., "Crystal Structures of Drugs: Advances in Determination, Prediction and Engineering," Nature Reviews Drug Discovery, 2004, vol. 3 (1), pp. 42-57.

Fernandez M., et al., "Characterization of Solid Dispersions of Piroxicam/Polyethylene Glycol 4000," International Journal of Pharmaceutics, 1992, vol. 84 (2), pp. 197-202.

Fernandez M., et al., "Dissolution Kinetics of Piroxicam in Solid Dispersions with Polyethylene Glycol 4000," International Journal of Pharmaceutics, 1993, vol. 98 (1-3), pp. 23-35.

File history for the U.S. Appl. No. 12/880,766, filed Sep. 13, 2010, 89 Pages.

File history for the U.S. Appl. No. 12/880,781, filed Sep. 13, 2010, 85 Pages.

Gidwani R., et al., "Spray-Dried Enteric Solid Dispersion as a Novel Oral Delivery System for a Pentapeptide Analog of Thymopentin," Drug Development and Industrial Pharmacy, 1992, vol. 18 (4), pp. 385-394.

Longer M., et al., "Preformulation Studies of a Novel HIV Protease Inhibitor, AG1343," Journal of Pharmaceutical Sciences, 1995, vol. 84 (9), pp. 1090-1093.

Office Action mailed Sep. 4, 2012 for European Application No. 10181268 filed Aug. 23, 2004.

Schmitt E., et al., "Moisture-dependent Crystallization of Amorphous Lamotrigine Mesylate," Journal of Pharmaceutical Sciences, 1996, vol. 85 (11), pp. 1215-1219.

Serajuddin A.T., et al., "Effect of Vehicle Amphiphilicity on the Dissolution and Bioavailability of a Poorly Water-Soluble Drug from Solid Dispersions," Journal of Pharmaceutical Sciences, 1988, vol. 77 (5), pp. 414-417.

Serajuddin A.T., et al., "Improved Dissolution of a Poorly Water-Soluble Drug from Solid Dispersions in Polyethylene Glycol: Polysorbate 80 Mixtures," Journal of Pharmaceutical Sciences, 1990, vol. 79 (5), pp. 463-464.

Sethia S., et al., "Solid Dispersions: Revival with Greater Possibilities and Applications in Oral Drug Delivery," Critical Reviews in Therapeutic Drug Carrier Systems, 2003, vol. 20 (2-3), pp. 215-247.

Sham H.L., et al., "ABT-378, A Highly Potent Inhibitor of the Human Immunodeficiency Virus Protease," Antimicrobial Agents and Chemotherapy, 1998, vol. 42 (12), pp. 3218-3224.

Stanley J.P., "Soft Gelatin Capsules" in: The Theory and Practice of Industrial Pharmacy, 3rd Edition, Lachman L., et al., eds., Lea and Febiger, 1986, pp. 398-412.

Taylor L.S., et al., "Spectroscopic Characterization of Interactions Between PVP and Indomethacin in Amorphous Molecular Dispersions," Pharmaceutical Research, 1997, vol. 14 (12), pp. 1691-1698.

Third Party Observations mailed Aug. 23, 2012 for European Application No. 10181250.1 filed Aug. 23, 2004.

Yoo S.U., et al., "Miscibility/stability Considerations in Binary Solid Dispersion Systems Composed of Functional Excipients Towards the Design of Multi-component Amorphous Systems," Journal of Pharmaceutical Sciences, 2009, vol. 98 (12), pp. 4711-4723.

Yoshioka M., et al., "Inhibition of Indomethacin Crystallization in Poly(vinylpyrrolidone) Coprecipitates," Journal of Pharmaceutical Sciences, 1995, vol. 84 (8), pp. 983-986.

Zhang G.G., et al., "Phase Transformation Considerations During Process Development and Manufacture of Solid Oral Dosage Forms," Advanced Drug Delivery Reviews, 2004, vol. 56 (3), pp. 371-390.

Breitenback J., et al., "Solid Dispersions by an Integrated Melt Extrusion System," Proceed. Int'l. symp. control. Rel. Bioact. Mater., 1998, vol. 25, pp. 804-804.

7113EP01—Opposition, Aug. 13, 2007, IMAK.

(56) References Cited

OTHER PUBLICATIONS

Abbott Global Citizenship Report—Ingenuity at Work, 2007, Table of Contents.
Abbott Laboratories: "Norvir" Product Labeling, NORVIR, Online, Mar. 2001.
Abbott Press Release [online], Jan. 24, 2007 [retrieved on Sep. 3, 2008]. Retrieved from the Internet< URL: http://www.abbott.com/global/url/printerFriendly/en_US/on>.
Abbott Press Release [online], Jan. 25, 2006 [retrieved on Sep. 3, 2008]. Retrieved from the Internet< URL: http://www.abbott.com/global/url/printerFriendly/en_US/on>.
Albers J., et al., "Mechanism of Drug Release from Polymethacrylate-Based Extrudates and Milled Strands Prepared by Hot-Melt Extrusion," European Journal of Pharmaceutics and Biopharmaceutics : Official Journal of Arbeitsgemeinschaft Fur Pharmazeutische Verfahrenstechnik E.V., 2009, vol. 71 (2), pp. 387-394.
Ambike A.A., et al., "Spray-Dried Amorphous Solid Dispersions of Simvastatin, a Low Tg Drug: In Vitro and in Vivo Evaluations," Pharmaceutical Research, 2005, vol. 22 (6), pp. 990-998.
Ambike A.A., et al., "Stability Study of Amorphous Valdecoxib," Stability Study of Amorphous Valdecoxib, 2004, vol. 282 (1-2), pp. 151-162.
Ansel C.H., et al., "Pharmaceutical Dosage Forms and Drug Delivery Systems", 7th Edition, Lippincott Williams & Wilkins, 1999, pp. 367-369.
Aungst B.J., et al., "Amphiphilic Vehicles Improve the Oral Bioavailability of a Poorly Soluble HIV Protease Inhibitor at High Doses," International Journal of Pharmaceutics, 1997, vol. 156, pp. 79-88.
Aungst B.J., et al., "Improved Oral Bioavailability of an HIV Protease Inhibitor Using Gelucire 44/14 and Labrasol Vehicles," 1994, vol. 87, pp. 49-54.
Awni W., et al., "Significantly Reduced Food Effect and Pharmacokinetic Variability with a Novel Lopinavir/ritonavir Tablet Formulation," Third IAS Conference on HIV Pathogenesis and Treatment, 2005, Rio de Janeiro, Brazil.
Bachynsky M.O., et al., "Factors Affecting the Efficiency of a Self-Emulsifying Oral Delivery System," Drug Development and Industrial Pharmacy, 1997, vol. 23 (8), pp. 809-816.
Banker G.S., et al., "Modern Pharmaceutics, Drugs and the Pharmaceutical Sciences," 2002, vol. 121 (Chapter. 11), pp. 335-380.
BASF Fine Chemicals, "ExAct Excipients & Actives fa Pharma", BASF, 2:1-16 (1999).
Bauer J., et al., "Ritonavir: An Extraordinary Example of Conformational Polymorphism," 2001, vol. 18 (6), pp. 859-866.
Benet L.Z., et al., "Using a Biopharmaceutics Drug Disposition Classification System to Predict Bioavailability and Elimination Characteristics of New Molecular Entities," Department of Biopharmaceutical Sciences, UCSF and Clinical Discovery, Bristol-Myers Squibb, 2006.
Boffito M., et al., "Clinical Use of Lopinavir/Ritonavir in a Salvage Therapy Setting: Pharmacokinetics and Pharmacodynamics," Aids, 2002, vol. 16 (15), pp. 2081-2083.
Bouma M.G., et al., "In Vitro and in Vivo Characteristics of Resorbable Gentamicin-polylactide in the Treatment of Osteomyelitis," Journal of Controlled Release, 2003, vol. 87, pp. 199-308.
Brazilian Interdisciplinary AIDS Association (ABIA) Opposition filed on Aug. 23, 2004, 26 pages.
Breitenbach J., et al., "Confocal Raman-Spectroscopy: Analytical Approach to Solid Dispersions and Mapping of Drugs," 1999, vol. 16 (7), pp. 1109-1113.
Breitenbach J., et al., "Two Concepts, One Technology: Controlled-Release Solid Dispersions Using Melt Extrusion (Meltrex)," Drugs and the Pharmaceutical Sciences, 2008, vol. 183, pp. 179-185.
Breitenbach J., et al., "Two Concepts, One Technology: Controlled-Release Solid Dispersions with Meltrex," Drugs and the Pharmaceutical Sciences, 2003, pp. 125-134.
Breitenbach J., "Melt Extrusion Can Bring New Benefits to HIV Therapy: The Example of Kaletra (R) Tablets," 2006, vol. 4 (2), pp. 61-64.
Breitenbach J., "Melt Extrusion: From Process to Drug Delivery Technology," Eur. J. of Pharm. & Biopharm., 2002, vol. 54 (2), pp. 107-117.
Buhler V., "Polyvinylpyrrolidone Excipients for Pharmaceuticals", Springer-Verlag, 2005, pp. 84-85, 92-93.
Center for Drug Evaluation and Research, Chemistry Reviews, 1999.
Chiou W.L., et al., "Pharmaceutical Applications of Solid Dispersion Systems," Journal of Pharmaceutical Sciences, 1971, vol. 60 (9), pp. 1281-1302.
CIPLA Opposition, Jul. 12, 2007, CIPLA.
CIPLA Pre-grant Oppositions Response mailed Aug. 11, 2011 for Indian Application No. 726/MUMNP/2009 filed Apr. 15, 2009.
Corrigan et al., "Surfactants in Pharmaceutical Products and Systems," EncycL of Pharm. Tech., pp. 2639-2653 , 2002.
Corrigan O.I., et al., "Amorphous forms of Thiazide Diuretics Prepared by Spray-Drying," International Journal of Pharmaceutics, 1984, vol. 18, pp. 195-200.
Corrigan O.I., et al., "Amorphous Spray-Dried Hydrofiumethiazide-Polyvinylpyrrolidone Systems: Physicochemical Properties," Journal of Pharmacy and Pharmacology , 1984, vol. 36 (4), pp. 217-221.
Corrigan O.I., et al., "Physicochemical Properties of Spray Dried Drugs: Phenobarbitone and Hydroflumethiazide," Physicochemical Properties of Spray Dried Drugs: Phenobarbitone and Hydroflumethiazide, 1983, vol. 9 (1-2), pp. 1-20.
Craig D.Q., "The Mechanisms of Drug Release from Solid Dispersions in Water-Soluble Polymers," International Journal of Pharmaceutics, 2002, vol. 231 (2), pp. 131-144.
Custodio J.M., et al., "Predicting Drug Disposition, Absorption/Elimination/Transporter Interplay and the Role of Food on Drug Absorption," 2008, vol. 60 (6), pp. 717-733.
Cvetkovic R.S., et al., "Lopinavir/Ritonavir: A Review of its Use in the Management of HIV Infection," Drugs, 2003, vol. 63 (8), pp. 769-802.
Decision by Indian Patent Office dated Dec. 30, 2010.
Dias L., et al., "Physical and Oral Dog Bioavailability Evaluation of ABT-538:PVP Co-precipitates, PDD 7475" in: Pharmaceutical Research, vol. 13 (9), Vincent H.L. Lee., et al., eds., Plenum Press, 1996, pp. S-351.
Eagling V.A., et al., "Differential Inhibition of Cytochrome P450 Isoforms by the Protease Inhibitors, Ritonavir, Saquinavir and Indinavir," 1997, vol. 44, pp. 190-194.
Eron J.J., et al., "Once-daily Versus Twice-daily Lopinavir/ritonavir in Antiretroviral-naive HIV-positive patients: a 48-week Randomized Clinical Trial," Journal of Infectious Diseases, 2004, vol. 189 (2), pp. 265-272.
European Opposition to EP Patent No. 1663183 filed by F. Hoffmann-La Roche AG on Apr. 2, 2012.
European Opposition to EP Patent No. 1663183 filed by Generics *UK Ltd. on Apr. 12, 2012.
European Opposition to EP Patent No. 1663183 filed by Hetero Drugs Ltd. on Apr. 13, 2012.
European Opposition to EP Patent No. 1663183 filed by Janssen on Apr. 13, 2012.
European Opposition to EP Patent No. 1663183 filed by Teva Pharmaceuticals on Apr. 13, 2012.
European Search Report for Application No. EP10159672, mailed on May 26, 2010, 2 pages.
European Search Report for Application No. EP10181250, mailed on Dec. 10, 2010, 2 pages.
European Search Report for Application No. EP10181264, mailed on Dec. 10, 2010, 2 pages.
European Search Report for Application No. EP10181268, mailed on Dec. 10, 2010, 2 pages.
European Search Report for Application No. EP10184860, mailed on Dec. 6, 2010, 2 pages.
Excipients & Activities for Pharma, ExAct, No. 20, May 2008.
Final Office Action mailed Mar. 12, 2009 for U.S. Appl. No. 11/691,819, filed Mar. 27, 2007.
Final Office Action mailed Mar. 17, 2010 for U.S. Appl. No. 12/190,252, filed Aug. 12, 2008.
Final Office Action mailed Dec. 22, 2010 for U.S. Appl. No. 11/939,640, filed Nov. 14, 2007.

(56) References Cited

OTHER PUBLICATIONS

Final Office Action mailed Dec. 31, 2008 for U.S. Appl. No. 11/064,467, filed Feb. 23, 2005.
Ford J.L., "The Current Status of Solid Dispersions," 1986, vol. 61 (3), pp. 69-88.
Formulation Technology, Emulsions, Suspensions, Solid Forms, Wiley-VCH, 2001, pp. 358-374.
Forster A., et al., "Characterization of Glass Solutions of Poorly Water-Soluble Drugs Produced by Melt Extrusion with Hydrophilic Amorphous Polymers," 2001, vol. 53 (3), pp. 303-315.
Forster A., et al., "Selection of Excipients for Melt Extrusion with Two Poorly Water-Soluble Drugs by Solubility Parameter Calculation and Thermal Analysis," 2001, vol. 226, pp. 147-161.
Franks F., "Scientific and Technological Aspects of Aqueous Glasses," Biophysical Chemistry, 2003, vol. 105 (2-3), pp. 251-261.
Friesen D.T., et al., "Hydroxypropyl Methylcellulose Acetate Succinate-Based Spray-Dried Dispersions: An Overview," Molecular Pharmaceutics, 2008, vol. 5 (6), pp. 1003-1019.
Garren K.W., et al., "Bioavailability of Generic Ritonavir and Lopinavir/Ritonavir Tablet Products in a Dog Model," Journal of Pharmaceutical Sciences, 2009, pp. 1-6.
Gubbins P.O., et al., "Pharmacokinetics and Safety of Oral Posaconazole in Neutropenic Stem Cell Transplant Recipients," Antimicrobial Agents and Chemotherpy, 2006, vol. 50 (6), pp. 1993-1999.
Hajratwala B.R., et al., "Effect of Aging on Hydrocortisone-Polyethylene Glycol 4000 and Hydrocortisone-Polyvinylpyrrolidone Dispersions," Journal of Pharmaceutical Sciences, 1984, vol. 73 (11), pp. 1539-1541.
Hancock B.C., et al., "Characteristics and Significance of the Amorphous State in Pharmaceutical Systems," Journal of Pharmaceutical Sciences, 1997, vol. 86 (1), pp. 1-12.
Hancock B.C., et al., "Molecular Mobility of Amorphous Pharmaceutical Solids Below Their Glass Transition Temperatures," Pharmaceutical Research, 1995, vol. 12 (6), pp. 799-806.
Hasegawa A., et al., "Application of Solid Dispersions with Enteric Coating Agents to Overcome Some Pharmaceutical Problems," Chemical & Pharmaceutical Bulletin, 1986, vol. 34 (5), pp. 2183-2190.
Hasegawa A., et al., "Solid Dispersion Obtained from Nifedipine and Enteric Coaling Agent. 1. Dissolution Behavior," Yakugaku Zasshi : Journal of the Pharmaceutical Society of Japan, 1984, vol. 104 (5), pp. 485-489.
Hasegawa A., et al., "Physical Properties of Solid Dispersions of Poorly Water-Soluble Drugs with Enteric Coating Agentsl," Chemical & Pharmaceutical Bulletin, 1985, vol. 33 (8), pp. 3429-3435.
Hasegawa A., et al., "Supersaturation Mechanism of Drugs from Solid Dispersions with Enteric Coating Agents," Chemical & Pharmaceutical Bulletin, 1988, vol. 36 (12), pp. 4941-4950.
Herausgeber, "Chemistry" Georg Thieme Verlag Stuttgart—NewYork, 1997, pp. 1549.
Hicks C., et al., "Long-term Safety and Durable Antiretroviral Activity of Lopinavir/Ritonavir in Treatment-naive Patients: 4 Year Follow-up Study," Aids, 2004, vol. 18 (5), pp. 775-779.
Hulsmann S., et al., "Melt extrusion—an alternative method for enhancing the eissolution rate of 17.beta.-estradiol hemihydrate," 2000, vol. 49, pp. 237-242.
I-Mak Opposition, Sep. 10, 2007, IMAK.
I-MAK Pre-Grant Opposition Response to Indian Patent Office for Application No. 339/MUMNP/2006 mailed Aug. 2, 2010. part—1-5.
IMAK Statement of Reply 339/MUMNP/2006—Exhibit D, Feb. 16, 2009, 117-160.
IMAK Statement of Reply 339/MUMNP/2006—Exhibits A to C, Feb. 16, 2009, pp. 47-116.
IMAK Statement of Reply 339/MUMNP/2006—Exhibits E to O, Feb. 16, 2009, pp. 161-244.
IMAK Statement of Reply 339/MUMNP/2006—Exhibits P To R, Feb. 16, 2009, pp. 245-307.
IMAK Statement of Reply 339/MUMNP/2006, pp. 1-46.
IMAK Third Party Observation against EP Application No. 04816820.7 dated Oct. 25, 2010.
International Preliminary Report on Patentability and Written Opinion for Application No. PCT/US2006/005944, mailed on Aug. 28, 2007, 7 pages.
International Search Report & Written Opinion from PCT/US2004/027401 dated May 8, 2006.
International Search Report for Application No. PCT/BR04/00119 mailed on Jan. 26, 2005, 1 page.
International Search Report for Application No. PCT/US2006/05944, mailed on Aug. 4, 2006, 4 pages.
International Search Report for Application No. PCT/US2007/084617, mailed on Sep. 18, 2008, 3 pages.
Jachowicz R., et al., "Solid Dispersions of Oxazepam," International Journal of Pharmaceutics, 1993, vol. 99, pp. 321-325.
John M., et al., "Hepatitis C Virus-associated Hepatitis Following Treatment of HIV-infected Patients with HIV Protease Inhibitors: An Immune Restoration Disease", Aids, 1998, vol. 12 (17), pp. 2289-2293.
Kaletra 2000.
Kaletra 2005 tablet label, Product Information.
Kanzer J., et al., "In situ formation of nanoparticles upon dispersion of melt extrudate formulations in aqueous medium assessed by asymmetrical flow field-flow fractionation," Journal of Pharmaceutical and Biomedical Analysis, 2010, 7 pages.
Karanth H., et al., "Industrially Feasible Alternative Approaches in the Manufacture of Solid Dispersions: A Technical Report," AAPS Pharmaceutical Science Technology, 2006, vol. 7(4), pp. 87.
Kaushal A.M., et al., "Amorphous Drug Delivery Systems: Molecular Aspects, Design, and Performance," Critical Reviews in Therapeutic Drug Carrier Systems, 2004, vol. 21 (3), pp. 133-193.
Kempf D.J., et al., "Abt-538 Is a Potent Inhibitor of Human Immunodeficiency Virus Protease and has High Oral Bioavailability in Humans," Proceedings of the National Academy of Sciences USA, 1995, vol. 92 (7), pp. 2484-2488.
Klein C.E., et al., "The Effect of Food on Ritonavir Bioavailability Following Administration of Ritonavir 100 mg Film-Coated Tablet in Healthy Adult Subjects", Abbott Laboratories,2008, Poster P247.
Klein C.E., et al., "The Tablet Formulation of Lopinavir/Ritonavir Provides Similar Bioavailability to the Soft-Gelatin Capsule Formulation With Less Pharmacokinetic Variability and Diminished Food Effect," Journal of Acquired Immune Deficiency Syndromes (1999), 2007, vol. 44 (4), pp. 401-410.
Kolter K., et al., "Hot-Melt Extrusion with BASF Pharma Polymers Extrusion Compendium," BASF—The Chemical Company, 2010, pp. 34-35.
Konno H., et al., "Influence of Different Polymers on the Crystallization Tendency of Molecularly Dispersed Amorphous Felodipine," Journal of Pharmaceutical Sciences , 2006, vol. 95 (12), pp. 2692-2705.
Kumar G.N., et al., "Cytochrome P450-Mediated Metabolism of the HIV-1 Protease Inhibitor Ritonavir (Abt-538) in Human Liver Microsomes," Journal of Pharmacology and Experimental Therapeutics, 1996, vol. 277 (1), pp. 423-431.
Law D., et al., "Physicochemical Considerations in the Preparation of Amorphous Ritonavir-poly(ethylene Glycol) 8000 Solid Dispersions," Journal of Pharmaceutical Sciences, 2001, vol. 90 (8), pp. 1015-1025.
Law D., et al., "Ritonavir—PEG 8000 Amorphous Solid Dispersions: In Vitro and In Vivo Evaluations," Journal of Pharmaceutical Sciences, 2004, vol. 93 (3), pp. 563-570.
Leuner C., et al., "Improving Drug Solubility for Oral Delivery Using Solid Dispersions," European Journal of Pharmaceutics and Biopharmaceutics : Official Journal of Arbeitsgemeinschaft Fur Pharmazeutische Verfahrenstechnik E.V., 2000, vol. 50 (1), pp. 47-60.
Lindenberg M., et al., "Classification of Orally Administered Drugs on the World Health Organization Model List for Essential Medicines According to the Biopharmaceutics Classification System," Journal of Pharmaceutics and Biopharmaceutics, 2004, vol. 58 (2), pp. 265-278.

(56) References Cited

OTHER PUBLICATIONS

Martin D., et al., "Method of Preparing an Orally Bioavailable Solid Formulation of an Insoluble Protease Inhibitor as a Coprecipitate with PVP and Other Excipients, PDD 7474" in: Pharmaceutical Research, vol. 13 (9), Vincent H.L. Lee., et al., eds., Plenum Press, 1996, pp. S-351.
Matrix Laboratories Opposition, Oct. 23, 2009, Matrix Laboratories.
Matrix Laboratories Pre-grant Opposition mailed Aug. 11, 2011 for Indian Application No. 726/MUMNP/2009 filed Apr. 15, 2009.
MatrixParagraph IV dated Jan. 29, 2009.
Mayersohn M., "Principles of Drug Absorption" in: Modern Pharmaceutics Drugs and the Pharmaceutical Sciences, Chapter 2, Banker G.S., et al., eds, 2002, pp. 23-66.
Miller D.A., et al., "Solid Dispersion Technologies," Drugs Pharm. Sci., 2008, vol. 172, pp. 451-491.
Modern Pharmaceutics, Drugs and the Pharmaceutical Sciences, 2002, vol. 121, Chapter 2, pp. 23-66.
Morissette S.L., et al., "Elucidation of Crystal form Diversity of the HIV Protease Inhibitor Ritonavir by High-throughput Crystallization," Proceedings of the National Academy of Sciences, 2003, vol. 100 (5), pp. 2180-2184.
Muller V.K., "Detection and Determination of Polyvinylpyrrolidone (PVP) and the Determination of Active Ingredients in Pharmaceutical Preparations Containing PVP," Pharmaceutica Acta Helvetiae, 1968, vol. 43, pp. 107-122.
Nakamichi K., et al.,, "Preparation of Nifedipine-Hydroxypropylmethylcellulose Phthalate Solid Dispersion by Twin Screw Extruder and its Evaluation," Yakuzaigaku, 1996, vol. 56 (1), pp. 15-22.
Nakamichi K., et al., "The Preparation of Enteric Solid Dispersions with Hydroxypropylmethylcellulose Acetate Succinate Using a Twin-Screw Extruder," Journal of Drug Delevery Science Technology, 2004, vol. 14 (3), pp. 193-198.
Niazi S.K., "Handbook of Pharmaceutical Manufacturing Formulations, Compressed Solid Products" 2004, vol. 1, CRC Press, pp. 60-101.
Non-Final Office Action mailed Aug. 6, 2009 for U.S. Appl. No. 11/064,467 filed, Feb. 23, 2005.
Non-Final Office Action mailed Apr. 8, 2010 for U.S. Appl. No. 11/939,640, filed Nov. 14, 2007.
Non-Final Office Action mailed Oct. 12, 2011 for U.S. Appl. No. 12/899,227, filed Oct. 6, 2010.
Non-Final Office Action mailed May 13, 2009 for U.S. Appl. No. 12/190,252, filed Aug. 12, 2008.
Non-Final Office Action mailed May 19, 2008 for U.S. Appl. No. 11/691,819, filed Mar. 27, 2007.
Office Action mailed Jan. 10, 2007 for European Application No. 04816820.7 filed Aug. 23, 2004.
Office Action mailed Mar. 19, 2008 for U.S. Appl. No. 10/925,442, filed Aug. 25, 2004.
Office Action mailed Mar. 19, 2009 for U.S. Appl. No. 10/925,442, filed Aug. 25, 2004.
Office Action mailed Jun. 22, 2009 for E.P. Application No. 048168207 filed Aug. 23, 2004.
Office Action mailed Oct. 22, 2009 for U.S. Appl. No. 11/691,819, filed Mar. 27, 2007.
Office Action mailed Mar. 24, 2008 for U.S. Appl. No. 11/064,467, filed Feb. 23, 2005.
OKASA Opposition, Mar. 25, 2009, OKASA.
Opposition Filed by Matrix Laboratories on Indian Application No. 676/MUMNP/2007 dated Apr. 28, 2011.
Opposition Filed by Matrix Laboratories on Indian Application No. 677/MUMNP/2007 dated Apr. 28, 2011.
Opposition Filed by Matrix Laboratories on Indian Application No. 1638 /MUMNP/2007 dated Apr. 28, 2011.
Order Granting Reexamination of US Patent No. 7364752 along with Reexam Non-Final Office Action dated Oct. 28, 2010.
Otsuka M., et al., "Hygroscopic Stability and Dissolution Properties of Spray-Dried Solid Dispersions of Furosemide with Eudragit," Journal of Pharmaceutical Sciences, 1993, vol. 82 (1), pp. 32-38.
Palmieri G.F., et al., "Characterization and Dissolution Studies of PEG 4000/fenofibrate solid Dispersions," S.T.P. Pharma Sciences, 1996, vol. 6 (3), pp. 188-194.
Peltonen et al., "Surface Pressure, Hysteresis, Interfacial Tension, and CMC of Four Sorbitan Monoesters at Water-Air, Water-Hexane and Hexane-Air Interfaces," Journal of Colloid and Interface Science, 2000, pp. 1-6, vol. 227.
Physicians Desk Reference, Tricor Capsules, Micronized [online], [retrieved on Aug. 2, 2000]. Retrieved from the Internet:< URL: http://www.pdrel.com/pdr/static.htm?path=pdrel/pdr/00404900.htm>.
Polymer Handbook, Brandrup J., et al., Eds., Interscience Publishers, 1975, Table of Contents, III-139-III-192.
Pouton C.W., "Formulation of poorly water-soluble drugs for oral administration: Physicochemical and physiological issues and the lipid formulation classification system," European Journal of Pharmaceutical Science, 2006, vol. 29 (3-4), pp. 278-287.
Qi S., et al., "Characterisation of Solid Dispersions of Paracetamol and EUDRAGIT E Prepared by Hot-Melt Extrusion Using Thermal, Microthermal and Spectroscopic Analysis," International Journal of Pharmaceutics, 2008, vol. 354 (1-2), pp. 158-167.
Rane Y., et al., "Effect of Hydrophilic Swellable Polymers on Dissolution Enhancement of Carbamazepine Solid Dispersions Studied Using Response Surface Methodology," American Association of Pharmaceutical Scientists Pharmacy Scientific Technologies, 2007, vol. 8 (2), pp. E1-E11.
ReExam—Non-Final Action mailed Oct. 28, 2010 for U.S. Appl. No. 95/000,568, filed Aug. 25, 2010.
ReExam Action Closing Prosecution mailed May 19, 2011 for U.S. Appl. No. 95/000,568, filed Aug. 25, 2010.
Request for Re-Examination on U.S. Appl. No. 95/000,568 mailed Aug. 25, 2010.
Requirement for Restriction mailed Jan. 18, 2010 for U.S. Appl. No. 11/939,640, filed Nov. 14, 2007.
Response to Inter Partes Reexamination dated Jun. 17, 2011 for U.S. Appl. No. 95/000,568, filed Aug. 25, 2010.
Response to Office Action mailed Apr. 4, 2008 for European Application No. 04816820.7 filed Aug. 23, 2004.
Response to Office Action mailed Aug. 10, 2009 for European Application No. 04816820.7 filed Aug. 23, 2004.
Riesen R., et al., "The Glass Transition Temperature Measured by Different TA Techniques, Part 2: Determination of Glass Transition Temperatures," USERCOM, 2003, 5 pages.
Rodriguez-Espinosa C., et al., "Dissolution Kinetics for Coprecipitates of Diflunisal with PVP K30," European Journal of Drug Metabolism and Pharmacokinetics, 1998, vol. 23 (2), pp. 109-112.
Rosenberg J., et al., "Meltrex-Formulations Containing Solid Solutions of Nearly Insoluble Drugs: Formation of Nanoparticles on Dissolution in Water," 28th International Symposium on Controlled Release of Bioactive Materials, 2001, vol. 1, pp. 738-739.
Rosenberg J., et al., "Novel Therapeutic Delivery System," Journal of Controlled Release, 2003, vol. 87, pp. 264-267.
Rossie R.C., et al., "Development and Validation of Dissolution Test for Ritonavir Soft Gelatin Capsules Based on in Vivo Data," International Journal of Pharmaceutics, 2007, vol. 338, pp. 119-124.
Rowe., "Polyoxyethylene Castor Oil Derivatives" Handbook of Pharmaceutical Excipients, 2002, pp. 474-478.
Royal, P.G., et al., "Characteristics of the Glass Transition of an Amorphous Drug Using Modulated DSC", Pharmaceutical Research, 15(7):1117-1121 (1998).
Saez-Llorens X., et al., "Forty-eight-week Evaluation of Lopinavir/Ritonavir, a New Protease Inhibitor, in Human Immunodeficiency Virus-infected Children," Journal of Pediatric Infectious Disease, 2003, vol. 22 (3), pp. 216-224.
Saleki-Gerhardt A., et al., "Non-Isothermal and Isothermal Crystallization of Sucrose from the Amorphous State," Pharmaceutical Research, 1994, vol. 11 (8), pp. 1166-1173.
Schwartz J.B., "Pharmaceutical Dosage Forms" vol. 2, Marcel Dekker, Inc., 1990, pp. 460-461.

(56) References Cited

OTHER PUBLICATIONS

Serajuddin A.T., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.
Serajuddin, A.T.M., "Bioavailability Enhancement of Poorly Water-Soluble Drugs by Solid Dispersion in Surface Active and Self-Emulsifying Vehicles," B.T. Gattefosse, vol. 90, 43-50, 1997.
Shamblin S.L., et al., "The Effects of Co-Lyophilized Polymeric Additives on the Glass Transition Temperature and Crystallization of Amorphous Sucrose," Journal of Thermal Analysis, 1996, vol. 47, pp. 1567-1579.
Simonelli A.P., et al., "Dissolution Rates of High Energy Polyvinylpyrrolidone (PVP) Sulfathiazole Coprecipitates," Journal of Pharmaceutical Sciences, 1969, vol. 58 (5), pp. 538-549.
Sinha S., et al., "Solid Dispersion As an Approach for Bioavailability Enhancement of Poorly Water-Soluble Drug Ritonavir," AAPS PharmSciTech, 2010, vol. 11 (2), pp. 518-527.
Six K., et al., "Characterization of Solid Dispersions of Itraconazole and Hydroxypropylmethylcellulose Prepared by Melt Extrusion, Part II," Pharmaceutical Research, 2003, vol. 20 (7), pp. 1047-1054.
Sjokvist E., et al., "Physicochemical Aspects of Drug Release. XIII. The effect of sodium dodecyl sulphate additions on the structure and Dissolution of a drug in solid dispersions," International Journal of Pharmaceutics, 1991, vol. 69, pp. 53-62.
Stenmark H.G., et al., "Biomimetic Synthesis of Macrolide/Ketolide Metabolites through a Selectiv N-Demethylation Reaction," Journal of Organic Chemistry, 2000, vol. 65 (12), pp. 3875-3876.
Takeuchi H., et al., "Spherical Solid Dispersion Containing Amorphous Tolbutamide Embedded in Enteric Coating Polymers or Colloid al Silica Prepared by Spray-Drying Technique," Chemical and Pharmaceutical Bulletin, 1987, vol. 35 (9), pp. 3800-3806.
Tanno F., et al., "Evaluation of Hypromellose Acetate Succinate (HPMCAS) as a Carrier in Solid Dispersions," Drug Development and Industrial Pharmacy, 2004, vol. 30 (1), pp. 9-17.
Teas J.P., "Graphic Analysis of Resin Solubilities," Journal of Paint Technology, 1968, vol. 40 (516), pp. 19-25.
Thayer A. M., "Finding Solutions, Custom manufacturers take on drug solubility issues to help pharmaceutical firms move products through development," Chemical & Engineering News, 2010, vol. 88 (22), pp. 13-18.
Tho I., et al., " Formation of Nano/Micro-Dispersions With Improved Dissolution Properties Upon Dispersion of Ritonavir Melt Extrudate in Aqueous Media," European Journal of Pharmaceutical Sciences, 2010, 8 pages.
U.S. Department of Health and Human Services Food and Drug Administration Center for Drug Evaluation and Research, Guidance for Industry, Aug. 2000, http://www.fda.gov/downloads/Drugs/GuidanceComplianceRegulatoryInformation/Guidances/ucm070246.pdf.
U.S. Appl. No. 09/438,994, James J. Fort, et al., filed Nov. 12, 1999.
U.S. Appl. No. 09/709,829, James J. Fort, et al., filed Nov. 10, 2000.
U.S. Appl. No. 11/691,819, James J. Fort, et al., filed Mar. 27, 2007.
U.S. Appl. No. 11/773,185 Joerge Rosenberg, et al., filed Jul. 3, 2007.
Vadnere M.K., "Coprecipitates and Melts" in: Encyclopedia of Pharmaceutical Technology, 2nd Edition, Swarbrick J., eds., Marcel Dekker, Inc, 2002, vol. 1, pp. 641-648.
Van Den Mooter G., et al., "Physical Stabilisation of Amorphous Ketoconazole in Solid Dispersions with Polyvinylpyrrolidone K25," European Journal of Pharmaceutical Sciences : Official Journal of the European Federation for Pharmaceutical Sciences, 2001, vol. 12 (3), pp. 261-269.
Vasconcelos T., et al., "Solid Dispersions as Strategy to Improve Oral Bioavailability of Poor Water Soluble Drugs," Drug Discovery Today, 2007, vol. 12 (23-24), pp. 1068-1075.
Verreck G., et al., "Characterization of Solid Dispersions of Itraconazole and Hydroxypropylmethylcellulose Prepared by Melt Extrusion—Part I ," International Journal of Pharmaceutics, 2003, vol. 251 (1-2), pp. 165-174.
Voigt R., et al., "Methods for determination of wett ability and their possible use in pharmaceutical technology", Pharmazie, 1975, 30 (11), 689-693.
Voigt R., "Pharmaceutical Technology" for Students and Professionals, 7th revised Edition, 2000, pp. 80-85.
Walmsley S., et al., "Lopinavir-ritonavir Versus Nelfinavir for the Initial Treatment of HIV Infection," New England Journal of Medicine, 2002, vol. 346 (26), pp. 2039-2046.
Yamagochi T., et al., "Improvement of Pharmaceutical Properties of 4"-O-(4-methoxyphenyl)Acetyltylosin Using Solid Dispersion with Carboxymethylethylcellulose," Yakuzaigaku, 1993, vol. 53 (4), pp. 221-228.
Yu L., "Amorphous Pharmaceutical Solids: Preparation, Characterization and Stabilization," Advanced Drug Delivery Reviews, 2001, vol. 48 (1), pp. 27-42.
Zhou D., et al., "A Calorimetric Investigation of Thermodynamic and Molecular Mobility Contributions to the Physical Stability of Two Pharmaceutical Glasses," Journal of Pharmaceutical Sciences, 2007, vol. 96 (1), pp. 71-83.
Zhou D., et al., "Physical Stability of Amorphous Pharmaceuticals Importance of Configurational Thermodynamic Quantities and Molecular Mobility," Journal of Pharmaceutical Sciences, 2002, vol. 91 (8), pp. 1863-1872.
Zhu T. et al., "New Tablet Formulation of Lopinavir/Ritonavir is Bioequivalent to the Capsule at a Dose 800/200 mg," 48th Interscience Conference on Antimicrobial Agents and Chemotherapy (ICAAC), Washington D.C., 2005.
Letter dated Mar. 29, 2013, from Hetero.
Breitenbach, J., "Melt extrusion: from process to drug delivery technology", Eur. J. Of Pharm. & Biopharm., 54:107-117 (2002).
Dias, L., et al., "Physical and Oral Dog Bioavailability Evaluaiton of ABT-538: PVP Co-Precipitates", poster (1996).
Garren, et al, Bioavailability of Generic Ritonavir and Lopinavir/ritonavir Tablet Products in Dog Model, Abbott Poster, May 20-23, 2008.
Martin, D., et al., "Method of Preparing an Orally Bioavailability Solid Formulation of an Insoluble Protease Inhibitor as a Coprecipitate with PVP and Other Excipients", Abbott Laboratories (1996).
Office Action dated Mar. 12, 2009 for U.S. Appl. No. 11/691,819, filed Mar. 27, 2007.
Mathys & Squire LLP, Letter to the European Patent Office, dated May 2, 2013).
Roxane Laboratories, Letter to Laura Schumacher, dated Jun. 28, 2013.

SOLID PHARMACEUTICAL DOSAGE FORM

This application is a continuation of U.S. patent application Ser. No. 12/880,781, filed Sep. 13, 2010, which is a divisional of U.S. patent application Ser. No. 10/925,442, filed on Aug. 25, 2004, which claims priority from U.S. Provisional Application Ser. No. 60/498,412, filed on Aug. 28, 2003, both of which are incorporated herein by reference in their entireties.

The present invention is directed to a solid pharmaceutical dosage form comprising at least one HIV protease inhibitor, and a process for preparing same.

The virus causing acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e., HIV-1 and HIV-2.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

A measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first pass effect. Aqueous solubility is one of the most important of these factors. Unfortunately, HIV protease inhibiting compounds typically are characterized by having poor aqueous solubility.

For a variety of reasons, such as patient compliance and taste masking, a solid dosage form is usually preferred over a liquid dosage form. In most instances however, oral solid dosage forms of a drug provide a lower bioavailability than oral solutions of the drug.

There have been attempts to improve the bioavailability provided by solid dosage forms by forming solid solutions of the drug. The term "solid solution" defines a system in a solid state wherein the drug is molecularly dispersed throughout a matrix such that the system is chemically and physically uniform or homogenous throughout. Solid solutions are preferred physical systems because the components therein readily form liquid solutions when contacted with a liquid medium such as gastric juice. The ease of dissolution may be attributed at least in part to the fact that the energy required for dissolution of the components from a solid solution is less than that required for the dissolution of the components from a crystalline or microcrystalline solid phase. If, however, the drug absorption in the gastrointestinal tract is slow the drug released from the solid solution may result in a high supersaturation and precipitate in the aqueous fluids of the gastrointestinal tract.

There is a continuing need for the development of improved oral solid dosage forms for HIV protease inhibitors which have suitable oral bioavailability and stability and which do not necessitate high vehicle volumes.

The present invention provides a solid pharmaceutical dosage form comprising a solid dispersion of at least one HIV protease inhibitor in at least one pharmaceutically acceptable water-soluble polymer and at least one pharmaceutically acceptable surfactant. In one embodiment, the pharmaceutically acceptable water-soluble polymer has a glass transition temperature (Tg) of at least about 50° C.

The term "solid dispersion" defines a system in a solid state (as opposed to a liquid or gaseous state) comprising at least two components, wherein one component is dispersed evenly throughout the other component or components. For example, the active ingredient or combination of active ingredients is dispersed in a matrix comprised of the pharmaceutically acceptable water-soluble polymer(s) and pharmaceutically acceptable surfactant(s). The term "solid dispersion" encompasses systems having small particles, typically of less than 1 μm in diameter, of one phase dispersed in another phase. When said dispersion of the components is such that the system is chemically and physically uniform or homogenous throughout or consists of one phase (as defined in thermodynamics), such a solid dispersion will be called a "solid solution" or a "glassy solution". A glassy solution is a homogeneous, glassy system in which a solute is dissolved in a glassy solvent. Glassy solutions and solid solutions of HIV protease inhibitors are preferred physical systems. These systems do not contain any significant amounts of active ingredients in their crystalline or microcrystalline state, as evidenced by thermal analysis (DSC) or X-ray diffraction analysis (WAXS).

In one embodiment of the present invention, the pharmaceutical dosage form is comprising from about 5 to about 30% by weight of the total dosage form (preferably from about 10 to about 25% by weight of the total dosage form) of an HIV protease inhibitor or a combination of HIV protease inhibitors, from about 50 to about 85% by weight of the total dosage form (preferably from about 60 to about 80% by weight of the total dosage form) of a water-soluble polymer (or any combination of such polymers), from about 2 to about 20% by weight of the total dosage form (preferably from about 3 to about 15% by weight of the total dosage form) of the surfactant (or combination of surfactants), and from about 0 to about 15% by weight of the total dosage form of additives.

HIV protease inhibiting compounds suitable for use in the present invention include for example, but are not limited thereto:

(2S,3S,5S)-5-(N—(N—((N-methyl-N-((2-isopropyl-4-thiazolyl)methyl)amino)carbonyl)-L-valinyl)amino-2-(N-((5-thiazoly)methoxy-carbonyl)-aminoyamino-1,6-diphenyl-3hydroxyhexane (ritonavir);

(2S,3S,5S)-2-(2,6-Dimethylphenoxyacetyl)amino-3-hydroxy-5-[2S-(1-tetrahydro-pyrimid-2-onyl)-3-methylbutanoyl]amino-1,6-diphenylhexane (ABT-378; lopinavir);

N-(2(R)-hydroxy-1(S)-indanyl)-2(R)-phenylmethyl-4(S)-hydroxy-5-(1-(4-(3-pyridyl-methyl)-2(S)—N'-(t-butykarboxamido)-piperazinyl))-pentaneamide (indinavir);

N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide(saquinavir);

5(S)-Boc-amino-4(S)-hydroxy-6-phenyl-2(R)phenylmethylhexanoyl-(L)-Val-(L)-Phe-morpholin-4-ylamide;

1-Naphthoxyacetyl-beta-methylthio-Ala-(2S,3S)3-amino-2-hydroxy-4-butanoyl-1,3-thiazolidine-4t-butylamide;

5-isoquinolinoxyacetyl-beta-methylthio-Ala-(2S,3S)-3amino-2-hydroxy-4-butanoyl-1,3-thiazolidine-4-tbutylamide;

[1S-[1R—(R-),2S*])—$N^{1[}$3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide;

amprenavir (VX-478); DMP-323; DMP-450; AG1343 (nelfinavir);

atazanavir (BMS 232,632);
tipranavir;
palinavir;
TMC-114;
RO033-4649;
fosamprenavir (GW433908);
P-1946;
BMS 186,318; SC-55389a; BILA 1096 BS; and U-140690, or combinations thereof.

In one embodiment, ritonavir (Abbott Laboratories, Abbott Park, Ill., USA) is an HIV protease inhibitor which may be formulated into the dosage form of the invention. This and other compounds as well as methods for preparing same are disclosed in U.S. Pat. Nos. 5,542,206 and 5,648,497, the disclosures of which are herein incorporated by reference. In a further embodiment, the present invention provides a dosage form wherein said HIV protease inhibitor is ritonavir or a combination of ritonavir and at least one other HIV protease inhibitor, the dosage form showing a dose-adjusted AUC of ritonavir plasma concentration in dogs of at least about 9 µg·h/ml/100 mg.

In another embodiment, lopinavir (Abbott Laboratories, Abbott Park, Ill., USA) is an HIV protease inhibitor which may be formulated into the dosage form of the invention. This and other compounds, as well as methods for preparing same, are identified in U.S. Pat. No. 5,914,332, the disclosure of which is herein incorporated by reference. In a further embodiment, the present invention provides a dosage form wherein said HIV protease inhibitor is lopinavir or a combination of lopinavir and at least one other HIV protease inhibitor, the dosage form showing a dose-adjusted AUC of lopinavir plasma concentration in dogs of at least about 20 µg·h/ml/100 mg (preferably at least about 22.5 µg·h/ml/100 mg, most preferred at least about 35 µg·h/ml/100 mg).

In yet another embodiment, nelfmavir mesylate (marketed under the tradename Viracept by Agouron Pharmaceuticals, Inc. in La Jolla, Calif.) is an HIV protease inhibitor which may be formulated into the dosage form of the invention.

The dosage forms of the present invention exhibit a release and absorption behaviour that is characterized by high attainable AUC, high attainable $C_{max}$ (maximum plasma concentration), and low $T_{max}$ (time to reach maximum plasma concentration).

In still another embodiment, the present invention provides a dosage form wherein said HIV protease inhibitor is a combination of ritonavir and lopinavir, the dosage form showing a dose-adjusted AUC of ritonavir plasma concentration in dogs of at least about 9 µg·h/ml/100 mg and a dose-adjusted AUC of lopinavir plasma concentration of at least about 20 µg·h/ml/100 mg (preferably at least about 22.5 µg·h/ml/100 mg, most preferred at least about 35 µg·h/ml/100 mg).

The term "AUC" means "Area Under the Curve" and is used in its normal meaning, i.e. as the area under the plasma concentration-time curve from 0 to 24 hours, where the dosage form has been administered orally to dogs (beagle) under non-fasting conditions. "Non-fasting condition" means that the dogs receive a nutritionally balanced daily ration during the pre-test period and the whole test period. The AUC has units of concentration times time. Once the experimental concentration-time points have been determined, the AUC may conveniently be calculated, e.g. by a computer program or by the trapezoidal method. All AUC data herein were dose adjusted to the 100 mg dose level. For the purposes herein, the AUC is determined within a dose range where the AUC increases proportionally with dose. Administration of 50 mg ritonavir or 200 mg lopinavir, respectively, to dogs is considered suitable for determining the AUC values as used herein.

The dosage forms according to the invention are characterized by an excellent stability and, in particular, exhibit high resistance against recrystallization or decomposition of the active ingredient(s). Thus, upon storage for 6 weeks at 40° C. and 75% humidity (e.g., when kept in high density polyethylene (HDPE) bottles without desiccant), the dosage forms according to the present invention usually do not exhibit any sign of crystallinity (as evidenced by DSC or WAXS analysis) and contain at least about 98% of the initial active ingredient content (as evidenced by HPLC analysis).

The term "pharmaceutically acceptable surfactant" as used herein refers to a pharma-ceutically acceptable non-ionic surfactant. In one embodiment, the dosage form is comprising at least one surfactant having an hydrophilic lipophilic balance (HLB) value of from about 4 to about 10, preferably from about 7 to about 9. The HLB system (Fiedler, H. B., Encyclopedia of Excipients, 5th ed., Aulendorf: ECV-Editio-Cantor-Verlag (2002)) attributes numeric values to surfactants, with lipophilic substances receiving lower HLB values and hydrophilic substances receiving higher HLB values. Surfactants having an HLB value of from about 4 to about 10 suitable for use in the present invention include for example, but are not limited thereto:

polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether;

polyethylene glycol fatty acid esters, e.g. PEG-200 monolaurate, PEG-200 dilaurate, PEG-300 dilaurate, PEG-400 dilaurate, PEG-300 distearate, PEG-300 dioleate;

alkylene glycol fatty acid mono esters, e.g. propylene glycol monolaurate (Lauroglycol®);

sucrose fatty acid esters, e.g. sucrose monostearate, sucrose distearate, sucrose monolaurate, sucrose dilaurate; or sorbitan fatty acid mono esters such as sorbitan mono laurate (Span® 20), sorbitan monooleate, sorbitan monopahnitate (Span® 40), or sorbitan stearate, or mixtures of one or more thereof.

The sorbitan mono fatty acid esters are preferred, with sorbitan mono laurate and sorbitan monopalmitate being particularly preferred.

Besides the surfactant having an HLB value of from about 4 to about 10, the dosage form may comprise additional pharmaceutically acceptable surfactants such as polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40) or polyethylenglycol 60 hydrogenated castor oil (Cremophor® RH 60); or block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, Poloxamer® 407 (BASF Wyandotte Corp.); or a mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20).

Where such additional surfactants are used, the surfactant having an HLB value of from about 4 to about 10 generally accounts for at least about 50% by weight, preferably at least about 60% by weight, of the total amount of surfactant used.

The water-soluble polymer employed in the present invention has a Tg of at least about 50° C., preferably at least about 60° C., most preferred from about 80° C. to about 180° C. Methods for determining Tg values of the organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers, i.e., that make up the polymer: $Tg=\Sigma W_i X_i$ where W is the weight percent of monomer i in the organic polymer, and X is the Tg value for the homopolymer derived from monomer i. Tg values for the homopolymers may be taken from "Polymer Handbook", 2nd Edition by J. Brandrup and E. H. Immergut, Editors, published by John Wiley & Sons, Inc., 1975.

Water-soluble polymers having a Tg as defined above allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids.

The water-soluble polymer comprised in the dosage form is a polymer that preferably has an apparent viscosity, when dissolved at 20° C. in an aqueous solution at 2% (w/v), of about 1 to about 5000 mPa·s. more preferably of about 1 to about 700 mPa·s, and most preferred of about 5 to about 100 mPa·s. Water-soluble polymers suitable for use in the present invention include for example, but are not limited thereto:

homopolymers and copolymers of N-vinyl lactams, especially homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropyhnethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate;

high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, oligo- and polysaccharides such as carrageenans, galactomannans and xanthan gum, or mixtures of one or more thereof.

Of these, homopolymers or copolymers of N-vinyl pyrrolidone, in particular a copolymer of N-vinyl pyrrolidone and vinyl acetate, are preferred. A particularly preferred polymer is a copolymer of about 60% by weight of the copolymer, N-vinyl pyrrolidone and about 40% by weight of the copolymer, vinyl acetate.

The dosage forms of the invention may contain at least one conventional additive, such as flow regulators, lubricants, bulking agents (fillers) and disintegrants. In general, the additive is contained in an amount of about 0.01 to about 15% by weight relative to the weight of the dosage form.

Various methods can be used for manufacturing the solid dosage forms according to the invention. These methods comprise the preparation of a solid solution of the HIV protease inhibitor or the combination of HIV protease inhibitors in a matrix of the water-soluble polymer and the surfactant, and shaping into the required tablet form. Alternatively, the solid solution product may be subdivided to granules, e.g. by grinding or milling, and the granules may subsequently be compacted to tablets.

Various techniques exist for preparing solid solutions including melt-extrusion, spray-drying and solution-evaporation with melt-extrusion being preferred.

The melt-extrusion process comprises the steps of preparing a homogeneous melt of the HIV protease inhibitor or the combination of HIV protease inhibitors, the water-soluble polymer and the surfactant, and cooling the melt until it solidifies. "Melting" means a transition into a liquid or rubbery state in which it is possible for one component to get embedded homogeneously in the other. Typically, one component will melt and the other components will dissolve in the melt thus forming a solution. Melting usually involves heating above the softening point of the water-soluble polymer. The preparation of the melt can take place in a variety of ways. The mixing of the components can take place before, during or after the formation of the melt. For example, the components can be mixed first and then melted or be simultaneously mixed and melted. Usually, the melt is homogenized in order to disperse the active ingredients efficiently. Also, it may be convenient first to melt the water-soluble polymer and then to mix in and homogenize the active ingredients.

Usually, the melt temperature is in the range of about 70 to about 250° C., preferably from about 80 to about 180° C., most preferred from about 100 to about 140° C.

The active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt.

Various additives may be included in the melt, for example flow regulators such as colloidal silica; lubricants, fillers, disintegrants, plasticizers, stabilizers such as antioxidants, light stabilizers, radical scavengers, stabilizers against microbial attack.

The melting and/or mixing takes place in an apparatus customary for this purpose. Particularly suitable ones are extruders or kneaders. Suitable extruders include single screw extruders, intermeshing screw extruders or else multi-screw extruders, preferably twin screw extruders, which can be corotating or counterrotating and, optionally, be equipped with kneading disks. It will be appreciated that the working temperatures will also be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt ranges from pasty to viscous. Shaping of the extrudate conveniently is carried out by a calender with two counter-rotating rollers with mutually matching depressions on their surface. A broad range of tablet forms can be attained by using rollers with different forms of depressions. Alternatively, the extrudate is cut into pieces, either before (hot-cut) or after solidification (cold-cut).

Optionally, the resulting solid solution product is milled or ground to granules. The granules may then be compacted. Compacting means a process whereby a powder mass comprising the granules is densified under high pressure in order to obtain a compact with low porosity, e.g. a tablet. Compression of the powder mass is usually done in a tablet press, more specifically in a steel die between two moving punches. Where a solid dosage form of the invention comprises a combination of more than one HIV protease inhibitor (or a combination of an HIV protease inhibitor with one or more other active ingredients) it is of course possible to separately prepare solid solution products of the individual active ingredients and to blend the milled or ground products before compacting.

At least one additive selected from flow regulators, disintegrants, bulking agents (fillers) and lubricants is preferably used in compacting the granules. Disintegrants promote a rapid disintegration of the compact in the stomach and keeps the granules which are liberated separate from one another. Suitable disintegrants are crosslinked polymers such as crosslinked polyvinyl pyrrolidone and crosslinked sodium carboxymethylcellulose. Suitable bulking agents (also referred to as "fillers") are selected from lactose, calcium hydrogenphosphate, microcrystalline cellulose (Avicell®), silicates, in particular silicium dioxide, magnesium oxide, talc, potato or corn starch, isomalt, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, and the like.

Various other additives may be used, for example dyes such as azo dyes, organic or inorganic pigments such as aluminum oxide or titanium dioxide, or dyes of natural origin; stabilizers such as antioxidants, light stabilizers, radical scavengers, stabilizers against microbial attack.

Dosage forms according to the invention may be provided as dosage forms consisting of several layers, for example laminated or multilayer tablets. They can be in open or closed form. "Closed dosage forms" are those in which one layer is completely surrounded by at least one other layer. Multilayer forms have the advantage that two active ingredients which are incompatible with one another can be processed, or that the release characteristics of the active ingredient(s) can be controlled. For example, it is possible to provide an initial dose by including an active ingredient in one of the outer layers, and a maintenance dose by including the active ingredient in the inner layer(s). Multilayer tablets types may be produced by compressing two or more layers of granules. Alternatively, multilayer dosage forms may be produced by a process known as "coextrusion". In essence, the process comprises preparation of at least two different melt compositions as explained above, and passing these molten compositions into a joint coextrusion die. The shape of the coextrusion die depends on the required drug form. For example, dies with a plain die gap, called slot dies, and dies with an annular slit are suitable.

In order to facilitate the intake of such a dosage form by a mammal, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. If desired, the film-coat may be an enteric coat. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. a Tween® type, and optionally a pigment, e.g. titanium dioxide or iron oxides. The film-coating may also comprise talc as anti-adhesive. The film coat usually accounts for less than about 5% by weight of the dosage form.

The exact dose and frequency of administration depends on the particular condition being treated, the age, weight and general physical condition of the particular patient as well as other medication the individual may be taking, as is well known to those skilled in the art.

Exemplary compositions of the present invention for combined administration of ritonavir/lopinavir are shown below in Table 1, and the values are % by weight.

TABLE 1

| | | | |
|---|---|---|---|
| Ritonavir | 18-22.5 | 4.17 | 4.17 |
| Lopinavir | in total | 16.67 | 16.67 |
| Copovidone (N-vinyl pyrrolidone/vinyl acetate copolymer 60:40) | 65-75 | 71.16 | 70.12 |
| Span 20 (Sorbitan monolaurate) | 4-10 | 7.0 | 5.02 |
| Cremophor RH40 (polyoxyethyleneglycerol oxystearate) | 0-10 | — | 3.02 |
| Colloidal silica | 0-3 | 1.0 | 1.0 |

Exemplary compositions of the invention for administration of ritonavir only are shown below in Table 2. The values are % by weight.

| | | |
|---|---|---|
| Ritonavir | 18-22.5 | 20.8 |
| Lopinavir | — | — |
| Copovidone (N-vinyl pyrrolidone/vinyl acetate copolymer 60:40) | 60-75 | 63.15 |
| Span 20 (Sorbitan monolaurate) | 5-15 in total | — |
| Cremophor RH40 (polyoxyethyleneglycerol oxystearate) | | 10.00 |
| PEG 6000 | 0-8 | 5.00 |
| Colloidal silica | 0-3 | 1.04 |

The above compositions are processed by melt extrusion. The resulting extrudates may be used as such or milled and compressed into tablets, preferably by the use of suitable tabletting aids such as sodium stearyl fumarate, colloidal silica, lactose, isomalt, calcium silicate, and magnesium stearate, cellulose or calcium hydrogenphosphate.

The following examples will serve to further illustrate the invention without limiting it.

PROTOCOL FOR THE ORAL BIOAVAILABILITY STUDIES

Dogs (beagle dogs, mixed sexes, weighing approximately 10 kg) received a balanced diet with 27% fat and were permitted water ad libitum. Each dog received a 100 µg/kg subcutaneous dose of histamine approximately 30 minutes prior to dosing. A single dose corresponding to about 200 mg lopinavir, about 50 mg ritonavir, or about 200 mg lopinavir and about 50 mg ritonavir, respectively, was administered to each dog. The dose was followed by approximately 10 milliliters of water. Blood samples were obtained from each animal prior to dosing and 0.25, 0.5, 1.0, 1.5, 2, 3, 4, 6, 8, 10, 12 and 24 hours after drug administration. The plasma was separated from the red cells by centrifugation and frozen (−30° C.)

until analysis. Concentrations of HIV protease inhibitors were determined by reverse phase HPLC with low wavelength UV detection following liquid-liquid extraction of the plasma samples. The area under the curve (AUC) was calculated by the trapezoidal method over the time course of the study. Each dosage form was evaluated in a group containing 8 dogs; the values reported are averages for each group of dogs.

Comparative Example

Copovidone (N-vinyl pyrrolidone/vinyl acetate copolymer 60:40; 78.17 parts by weight) was mixed with ritonavir (4.16 parts by weight), lopinavir (16.67 parts by weight) and colloidal silica (1.0 part by weight). The powdery mixture was then fed into a twin-screw extruder (screw diameter 18 mm) at a rate of 2.0 kg/h and a melt temperature of 133° C. The clear, fully transparent melt was fed to a calender with two counter-rotating rollers having mutually matching cavities on their surfaces. Tablets of 1080 mg were thus obtained. DSC and WAXS analysis did not reveal any evidence of crystalline drug material in the formulation.

The dose-adjusted AUC in dogs was 0.52 µg·h/ml/100 mg for ritonavir and 4.54 µg·h/ml/100 mg for lopinavir. This example shows that solid solutions of HIV protease inhibitors without added surfactant yield a very poor bioavailabilty.

Example 1

Copovidone (N-vinyl pyrrolidone/vinyl acetate copolymer 60:40; 68.17 parts by weight) was blended with Cremophor RH40 (polyoxyethyleneglycerol oxystearate; 10.00 parts by weight) in a Diosna high-shear mixer. The resulting granules were mixed with ritonavir (4.17 parts by weight), lopinavir (16.67 parts by weight) and colloidal silica (1.00 parts by weight). The powdery mixture was then fed into a Leistritz Micro 18 twin-screw extruder at a rate of 2.3 kg/h and a melt temperature of 126° C. The extrudate was cut into pieces and allowed to solidify. The extruded pieces were milled using a high impact universal mill. The milled material (86.49 parts by weight) was blended in a bin blender with lactose monohydrate (6.00 parts by weight), crosslinked PVP (6.00 parts by weight), colloidal silica (1.00 part by weight) and magnesium stearate (0.51 parts by weight). The powdery blend was compressed to tablets of 1378.0 mg on a Fette E 1 single punch tablet press. The tablets were then film-coated in a coating pan by spraying an aqueous dispersion for film coating (Opadry, available from Colorcon) at a temperature of 60° C.

The dose-adjusted AUC in dogs was 0.60 µg·h/ml/100 mg for ritonavir and 7.43 µg·h/ml/100 mg for lopinavir. This example shows that inclusion of a surfactant into solid solutions of HIV protease inhibitors improves the bioavailabilty attained.

Example 2

Copovidone (N-vinyl pyrrolidone/vinyl acetate copolymer 60:40; 853.8 parts by weight) was blended with Span 20 (Sorbitan monolaurate; 83.9 parts by weight) in a Diosna high-shear mixer. The resulting granules were mixed with ritonavir (50 parts by weight), lopinavir (200 parts by weight) and colloidal silica (12 parts by weight). The powdery mixture was then fed into a twin-screw extruder (screw diameter 18 nun) at a rate of 2.1 kg/h and a melt temperature of 119° C. The extrudate was fed to a calender with two counter-rotating rollers having mutually matching cavities on their surfaces. Tablets of 1120 mg were thus obtained.

The dose-adjusted AUC in dogs was 10.88 µg·h/ml/100 mg for ritonavir and 51.2 µg·h/ml/100 mg for lopinavir. This example shows that inclusion of a surfactant having an HLB of 4 to 10 into solid solutions of HIV protease inhibitors markedly improves the bioavailability attained.

Example 3

Example 2 was repeated, however, the extrudate was cut into pieces and allowed to solidify. The extruded pieces were milled to a particle size of about 250 µm, using a high impact universal mill. The milled material was blended in a bin blender with sodium stearyl fumarate (12.3 parts by weight) and colloidal silica (8.0 parts by weight) for 20 min. The powdery blend was compressed on a rotary tablet machine with 3 punches (6500 tablets/h). The tablets were then film-coated in a coating pan by spraying an aqueous dispersion for film coating (Opadry) at a temperature of 60° C.

The dose-adjusted AUC in dogs was 14.24 µg·h/ml/100 mg for ritonavir and 52.2 µg·h/ml/100 mg for lopinavir.

Example 4

Copovidone (N-vinyl pyrrolidone/vinyl acetate copolymer 60:40; 841.3 parts by weight) was blended with Cremophor RH40 (polyoxyethyleneglycerol oxystearate; 36.2 parts by weight), Span 20 (Sorbitan monolaurate; 60.2 parts by weight) in a Diosna high-shear mixer. The resulting granules were mixed with ritonavir (50 parts by weight), lopinavir (200 parts by weight) and colloidal silica (12 parts by weight). The powdery mixture was then fed into a twin-screw extruder (screw diameter 18 mm) at a rate of 2.1 kg/h and a melt temperature of 114° C. The extrudate was fed to a calender with two counter-rotating rollers having mutually matching cavities on their surfaces. Tablets of 1120 mg were thus obtained.

The dose-adjusted AUC in dogs was 10.96 µg·h/ml/100 mg for ritonavir and 46.5 µg·h/ml/100 mg for lopinavir. This example shows that a combination of a surfactant having an HLB of 4 to 10 and a further surfactant can successfully be used.

Example 5

Example 4 was repeated, however, the extrudate was cut into pieces and allowed to solidify. The extruded pieces were milled to a particle size of about 250 µm, using a high impact universal mill. The milled material was blended in a bin blender with sodium stearylfumarate (13.9 parts by weight), colloidal silica (7.0 parts by weight), isomalt DC100 (159.4 parts by weight) and calcium silicate (7.0 parts by weight) for 20 min. The blend was compressed and film-coated as described in example 1.

The dose-adjusted AUC in dogs was 10.38 µg·h/ml/100 mg for ritonavir and 42.7 µg·h/ml/100 mg for lopinavir.

Example 6

Copovidone (N-vinyl pyrrolidone/vinyl acetate copolymer 60:40; 683.3 parts by weight) was blended with Span 40 (sorbitan monopalmitate; 67.2 parts by weight) in a Diosna high-shear mixer. The resulting granules were mixed with lopinavir (200 parts by weight) and colloidal silica (9.6 parts by weight). The powdery mixture was then fed into a twin-screw extruder (screw diameter 18 mm) at a rate of 2.1 kg/h and a melt temperature of 119° C. The extrudate was cut into pieces and allowed to solidify. The extruded pieces were milled using a high impact universal mill. The milled material was blended in a bin blender with sodium stearylfumarate (7.9 parts by weight), colloidal silica (11.3 parts by weight), isomalt DC100 (129.1 parts by weight) and sodium dodecyl sulfate (15.6 parts by weight). The blend was compressed and film-coated as described in example 1.

Tablets corresponding to 200 mg lopinavir were coadministered to dogs together with 50 mg ritonavir. The dose-adjusted AUC of lopinavir was 38.8 μg·h/ml/100 mg.

Example 7

Copovidone (N-vinyl pyrrolidone/vinyl acetate copolymer 60:40; 151.5 parts by weight) was blended with Cremophor RH40 (24 parts by weight) and PEG 6000 (12 parts by weight) in a Diosna high-shear mixer. The resulting granules were mixed with ritonavir (50 parts by weight) and colloidal silica (2.4 parts by weight). The powdery mixture was then fed into a twin-screw extruder and was melt-extruded. The extrudate was cut into pieces and allowed to solidify. The extruded pieces were milled using a high impact universal mill. The milled material was blended in a bin blender with colloidal silica (1.4 parts by weight), isomalt DC100 (31.9 parts by weight) and calcium silicate (4.2 parts by weight). The blend was compressed and film-coated as described in example 1.

The dose-adjusted AUC in dogs was 9.98 μg·h/ml/100 mg.

What is claimed is:

1. A method of treating HIV, comprising administering a solid pharmaceutical dosage form to a patient in need thereof, wherein the dosage form comprises ritonavir formulated in solid dispersion, and said solid dispersion comprises (1) a pharmaceutically acceptable surfactant having an HLB value of from 4 to 10, or a combination of pharmaceutically acceptable surfactants having an HLB value of from 4 to 10, and (2) a pharmaceutically acceptable water-soluble polymer having a Tg of at least 50° C., or a combination of pharmaceutically acceptable water-soluble polymers having a Tg of at least 50° C., and wherein the dosage form comprises from 50% to 85% by weight of the total dosage form of said water-soluble polymer or said combination of water-soluble polymers.

2. The method of claim 1, wherein said solid dispersion is glassy solution or solid solution.

3. The method of claim 2, wherein said solid dispersion comprises a copolymer of N-vinyl pyrrolidone and vinyl acetate.

4. The method of claim 3, wherein said solid dispersion comprises a sorbitan mono fatty acid ester.

5. The method of claim 2, wherein said solid dispersion comprises copovidone and sorbitan monolaurate.

6. The method of claim 2, wherein said surfactant or said combination of surfactants is present in an amount of from 2% to 20% by weight of the total dosage form.

7. The method of claim 2, wherein the dosage form comprises at least one additive selected from flow regulators, disintegrants, bulking agents or lubricants.

8. The method of claim 2, wherein the dosage from contains, upon storage for 6 weeks at 40° C. and 75% humidity, at least 98% of the initial content of ritonavir.

9. The method of claim 2, wherein the dosage form has a dose-adjusted AUC, in dogs under non-fasting conditions, of ritonavir plasma concentration of at least 9 μg h/ml/100 mg.

10. The method of claim 1, wherein the dosage form further comprises lopinavir formulated in solid dispersion.

11. The method of claim 2, wherein the dosage form further comprises lopinavir formulated in solid solution or glassy solution.

12. The method of claim 2, wherein the dosage form further comprises lopinavir formulated in solid solution or glassy solution which comprises (i) a pharmaceutically acceptable surfactant having an HLB value of from 4 to 10, or a combination of pharmaceutically acceptable surfactants having an HLB value of from 4 to 10, and (ii) a pharmaceutically acceptable water-soluble polymer having a Tg of at least 50° C. or a combination of pharmaceutically acceptable water-soluble polymers having a Tg of at least 50° C.

13. The method of claim 1, wherein said solid dispersion comprises said pharmaceutically acceptable surfactant and said pharmaceutically acceptable water-soluble polymer, and said pharmaceutically acceptable water-soluble polymer is present in an amount of from 50% to 85% by weight of the total dosage form.

14. The method of claim 2, wherein said solid dispersion comprises said pharmaceutically acceptable surfactant and said pharmaceutically acceptable water-soluble polymer, and said pharmaceutically acceptable water-soluble polymer is present in an amount of from 50% to 85% by weight of the total dosage form.

15. The method of claim 2, wherein the dosage form comprises a copolymer of N-vinyl pyrrolidone and vinyl acetate in an amount of from 50% to 85% by weight of the total dosage form.

16. The method of claim 15, wherein the dosage form comprises a sorbitan mono fatty acid ester in an amount of from 2% to 20% by weight of the total dosage form.

17. The method of claim 2, wherein the dosage form comprises copovidone in an amount of from 50% to 85% by weight of the total dosage form, and sorbitan monolaurate in an amount of from 2% to 20% by weight of the total dosage form.

18. The method of claim 17, wherein the dosage form further comprises lopinavir formulated in solid dispersion.

19. The method of claim 17, wherein the dosage form further comprises lopinavir formulated in solid solution or glassy solution.

20. The method of claim 17, wherein the dosage form further comprises lopinavir formulated in solid solution or glassy solution which comprises copovidone and sorbitan monolaurate.

* * * * *

UNITED STATES PATENT AND TRADEMARK OFFICE
CERTIFICATE OF CORRECTION

PATENT NO. : 8,691,878 B2  
APPLICATION NO. : 13/674799  
DATED : April 8, 2014  
INVENTOR(S) : Rosenberg et al.

Page 1 of 1

It is certified that error appears in the above-identified patent and that said Letters Patent is hereby corrected as shown below:

In the Specification

Column 02, line 49, detailed description: "butykarboxamido" to read as --butylcarboxamido--

Column 04, line 39, detailed description: "monopahnitate" to read as --monopalmitate--

Column 05, line 38, detailed description: "hydroxypropyhnethylcellulose" to read as --hydroxypropylmethylcellulose--

In the Claims

Column 12, line 04, claim 8: "from" to read as --form--

Signed and Sealed this  
Fourth Day of August, 2015

Michelle K. Lee  
*Director of the United States Patent and Trademark Office*